US011110277B2

(12) United States Patent
Kaula et al.

(10) Patent No.: US 11,110,277 B2
(45) Date of Patent: *Sep. 7, 2021

(54) SYSTEM AND METHOD OF PERFORMING COMPUTER ASSISTED STIMULATION PROGRAMMING (CASP) WITH A NON-ZERO STARTING VALUE CUSTOMIZED TO A PATIENT

(71) Applicant: CIRTEC MEDICAL CORPORATION, Brooklyn Park, MN (US)

(72) Inventors: Norbert Kaula, Arvada, CO (US); Yohannes Iyassu, Denver, CO (US)

(73) Assignee: CIRTEC MEDICAL CORP., Brooklyn Park, MN (US)

( * ) Notice: Subject to any disclaimer, the term of this patent is extended or adjusted under 35 U.S.C. 154(b) by 322 days.

This patent is subject to a terminal disclaimer.

(21) Appl. No.: 16/131,393

(22) Filed: Sep. 14, 2018

(65) Prior Publication Data

US 2019/0009092 A1    Jan. 10, 2019

Related U.S. Application Data

(63) Continuation of application No. 15/043,794, filed on Feb. 15, 2016, now Pat. No. 10,076,667.

(Continued)

(51) Int. Cl.
*A61N 1/36* (2006.01)
*A61N 1/372* (2006.01)
(Continued)

(52) U.S. Cl.
CPC ....... *A61N 1/36132* (2013.01); *A61N 1/3605* (2013.01); *A61N 1/36014* (2013.01);
(Continued)

(58) Field of Classification Search
CPC .......................... A61N 1/36132; A61N 1/3605
See application file for complete search history.

(56) References Cited

U.S. PATENT DOCUMENTS 4,245,641 A   1/1981 Mann et al.
4,503,863 A   3/1985 Katims
(Continued)

FOREIGN PATENT DOCUMENTS

EP   1 048 317 A2   11/2000
EP   1 048 317 A3   3/2003
(Continued)

OTHER PUBLICATIONS

European Patent Office, "European Search Report" for Application No. 16172698.9, dated Sep. 8, 2016, 8 pages.
(Continued)

*Primary Examiner* — George R Evanisko
(74) *Attorney, Agent, or Firm* — Haynes and Boone, LLP; J. Andrew Lowes; Eric Q. Li

(57) ABSTRACT

A non-zero starting value for ramping up a stimulation parameter for an electrical stimulation to be delivered to a patient is determined. The non-zero starting value is customized to the patient. A pulse generator is caused to generate the electrical stimulation, which is delivered to the patient via an implanted lead. The pulse generator is caused to ramp up, from the determined non-zero starting value and toward a predefined maximum limit value, the stimulation parameter for a plurality of electrode contacts on the lead. Feedback is received from the patient in response to the ramping up. The feedback is received via an electronic patient feedback device. Based on the ramping up and the received feedback from the patient, a perception threshold is determined for each of the plurality of electrode contacts. The perception threshold is a value of the stimulation parameter that corresponds to the patient feeling the electrical stimulation.

20 Claims, 25 Drawing Sheets

Related U.S. Application Data

(60) Provisional application No. 62/181,827, filed on Jun. 19, 2015, provisional application No. 62/173,118, filed on Jun. 9, 2015.

(51) Int. Cl.
- *G16H 40/63* (2018.01)
- *G16H 20/30* (2018.01)
- *G06F 19/00* (2018.01)
- *G16H 20/40* (2018.01)
- *G16H 40/67* (2018.01)
- *G16H 50/50* (2018.01)

(52) U.S. Cl.
CPC ......... *A61N 1/37247* (2013.01); *G06F 19/00* (2013.01); *G16H 20/30* (2018.01); *G16H 20/40* (2018.01); *G16H 40/63* (2018.01); *G16H 40/67* (2018.01); *G16H 50/50* (2018.01); *A61N 1/36007* (2013.01); *A61N 1/36107* (2013.01); *A61N 1/36185* (2013.01); *A61N 1/37264* (2013.01)

(56) References Cited

U.S. PATENT DOCUMENTS

| | | | |
|---|---|---|---|
| 5,725,560 A | 3/1998 | Brink | |
| 6,275,735 B1 | 8/2001 | Jarding et al. | |
| 6,505,074 B2 | 1/2003 | Boveja et al. | |
| 7,174,213 B2 | 2/2007 | Pless | |
| 7,263,402 B2* | 8/2007 | Thacker | A61N 1/36071 607/46 |
| 7,450,992 B1* | 11/2008 | Cameron | A61N 1/0551 607/46 |
| 7,601,116 B2 | 10/2009 | Fischell et al. | |
| 7,881,783 B2 | 2/2011 | Bonde et al. | |
| 8,060,208 B2 | 11/2011 | Kilgore et al. | |
| 8,095,216 B1 | 1/2012 | Moulder et al. | |
| 8,112,154 B2 | 2/2012 | Rezai et al. | |
| 8,260,412 B2 | 9/2012 | Krause et al. | |
| 8,688,217 B2 | 4/2014 | Aghassian et al. | |
| 8,751,016 B2 | 6/2014 | Schleicher et al. | |
| 8,761,897 B2 | 6/2014 | Kaula et al. | |
| 8,805,515 B2 | 8/2014 | York et al. | |
| 9,014,813 B2 | 4/2015 | Foutz et al. | |
| 9,144,680 B2 | 9/2015 | Kaula et al. | |
| 10,076,667 B2* | 9/2018 | Kaula | G06F 19/00 |
| 2004/0098065 A1 | 5/2004 | Hagglof et al. | |
| 2006/0122660 A1 | 6/2006 | Boveja et al. | |
| 2006/0259099 A1 | 11/2006 | Goetz | |
| 2007/0097593 A1 | 5/2007 | Armstrong | |
| 2007/0213790 A1 | 9/2007 | Nolan | |
| 2007/0250121 A1 | 10/2007 | Miesel | |
| 2009/0024186 A1 | 1/2009 | Brockway | |
| 2010/0280575 A1 | 11/2010 | Carbunaru et al. | |
| 2011/0307032 A1 | 12/2011 | Goetz et al. | |
| 2012/0101326 A1 | 4/2012 | Simon et al. | |
| 2012/0310299 A1 | 12/2012 | Kaula | |
| 2012/0310300 A1 | 12/2012 | Kaula | |
| 2012/0310305 A1 | 12/2012 | Kaula | |
| 2013/0268019 A1 | 10/2013 | Gupta | |
| 2013/0296966 A1 | 11/2013 | Wongsarnpigoon et al. | |
| 2013/0304152 A1 | 11/2013 | Bradley et al. | |
| 2014/0046397 A1 | 2/2014 | Rohrer | |
| 2014/0046398 A1 | 2/2014 | Sachs et al. | |
| 2014/0067013 A1 | 3/2014 | Kaula et al. | |
| 2014/0067019 A1 | 3/2014 | Kothandaraman et al. | |
| 2014/0067020 A1 | 3/2014 | Kaula et al. | |
| 2014/0068758 A1 | 3/2014 | Kaula et al. | |
| 2014/0180361 A1 | 6/2014 | Burdick et al. | |
| 2014/0222102 A1 | 8/2014 | Lemus et al. | |
| 2014/0243926 A1 | 8/2014 | Carcieri | |
| 2014/0249599 A1 | 9/2014 | Kaula et al. | |
| 2015/0032181 A1* | 1/2015 | Baynham | A61N 1/3615 607/46 |
| 2015/0039047 A1 | 2/2015 | Parker | |
| 2015/0119958 A1 | 4/2015 | Li et al. | |
| 2015/0134027 A1 | 5/2015 | Kaula et al. | |
| 2015/0134028 A1 | 5/2015 | Kaula et al. | |
| 2016/0022996 A1 | 1/2016 | Kaula et al. | |
| 2016/0045747 A1 | 2/2016 | Jiang | |
| 2016/0121126 A1 | 5/2016 | Marnfeldt | |
| 2017/0203102 A1 | 7/2017 | Grandhe | |

FOREIGN PATENT DOCUMENTS

| | | |
|---|---|---|
| EP | 2 567 729 | 3/2013 |
| WO | WO 2006/107848 | 10/2006 |
| WO | WO 2009/097224 | 8/2009 |
| WO | WO 2011/156288 | 12/2011 |

OTHER PUBLICATIONS

European Patent Office, "European Search Report" for Application No. 16172706.0, dated Oct. 10, 2016, 7 pages.
European Patent Office, "European Search Report" for Application No. 16172702.9, dated Oct. 26, 2016, 8 pages.
European Patent Office, "European Search Report" for Application No. 16173541.0, dated Nov. 3, 2016, 6 pages.
European Patent Office, "Communication Pursuant to Article 94(#) EPC" for Application No. 16172702.9, dated Nov. 15, 2018.

* cited by examiner

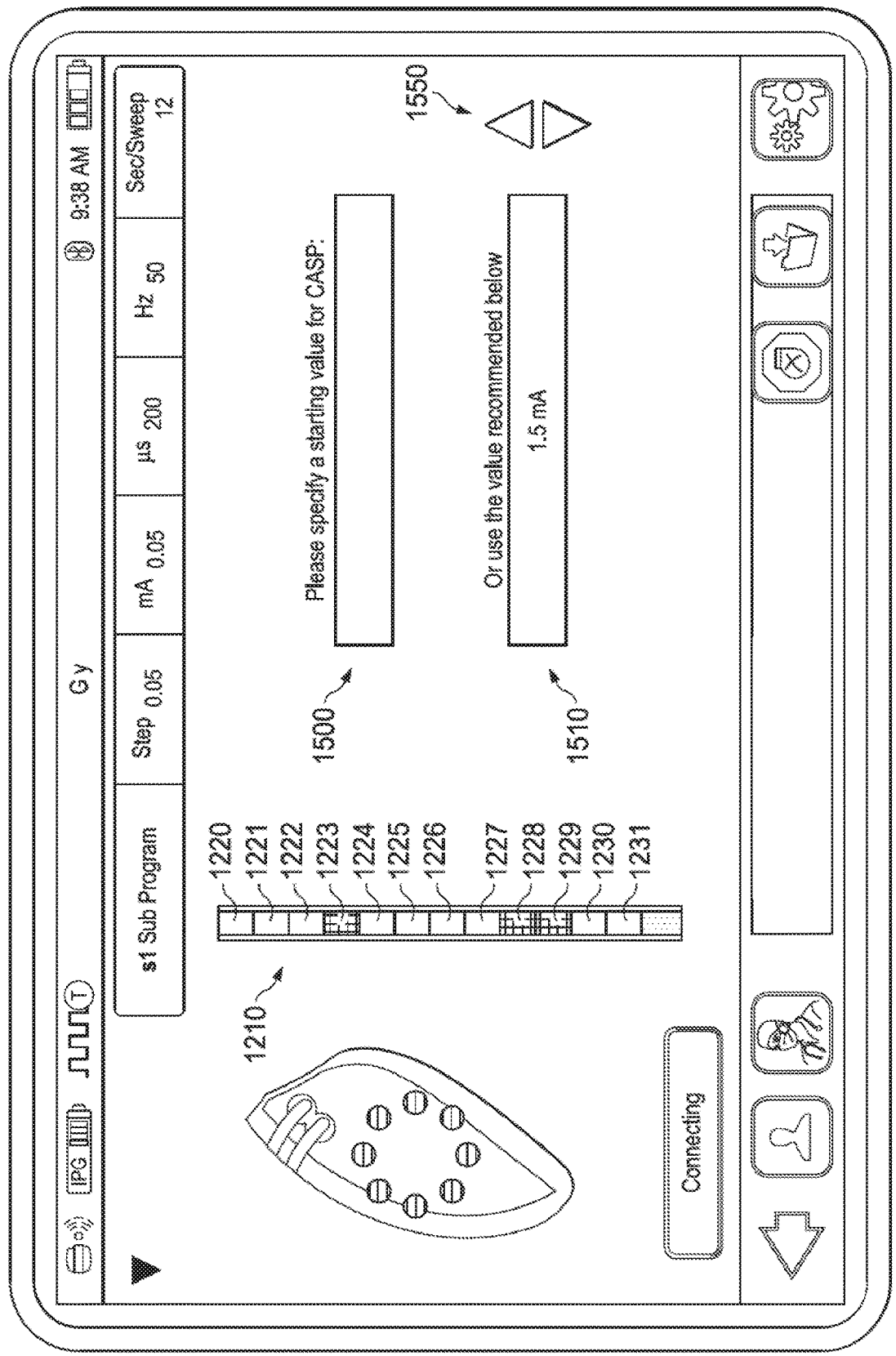

SYSTEM AND METHOD OF PERFORMING COMPUTER ASSISTED STIMULATION PROGRAMMING (CASP) WITH A NON-ZERO STARTING VALUE CUSTOMIZED TO A PATIENT

PRIORITY DATA

The present application is a continuation application of U.S. patent application Ser. No. 15/043,794, filed on Feb. 15, 2016, which claims priority to U.S. Provisional Patent Application No. 62/173,118, filed on Jun. 9, 2015, and to U.S. Provisional Patent Application No. 62/181,827, filed on Jun. 19, 2015, the disclosures of each which are hereby incorporated by reference in their respective entireties.

BACKGROUND

The invention relates to a stimulation system, such as a spinal cord stimulation (SCS) system, having a tool for programming an electrical stimulation generator, such as an implantable pulse generator (IPG), of the system. The invention also relates to a method for developing a protocol for the stimulation system.

A spinal cord stimulator is a device used to provide electrical stimulation to the spinal cord or spinal nerve neurons for managing pain. The stimulator includes an implanted or external pulse generator and an implanted medical electrical lead having one or more electrodes at a distal location thereof. The pulse generator provides the stimulation through the electrodes via a body portion and connector of the lead. Spinal cord stimulation programming is defined as the discovery of the stimulation electrodes and parameters that provide the best possible pain relief (or paresthesia) for the patient using one or more implanted leads and its attached IPG. The programming is typically achieved by selecting individual electrodes and adjusting the stimulation parameters, such as the shape of the stimulation waveform, amplitude of current in mA (or amplitude of voltage in V), pulse width in microseconds, frequency in Hz, and anodic or cathodic stimulation.

With newer medical electrical leads having an increased number of electrodes, the electrode and parameter combination increases exponentially. This results in a healthcare professional, such as a clinician, requiring a substantial amount of time for establishing a manually created protocol for providing therapeutic spinal cord stimulation. Therefore, a manual approach for creating a protocol is not an optimal solution for the SCS system.

SUMMARY

Numerous embodiments of the invention provide a method and system for programming an SCS system with a substantially reduced time requirement and increased accuracy. More specifically, in numerous embodiments, a sweep process is used with the electrodes of an implanted medical lead to determine the proper SCS program (also referred to herein as an SCS protocol) for providing the best possible pain relieve for the patient.

In one embodiment, the present disclosure provides a programming device for establishing a protocol for a plurality of electrodes in one or more medical leads coupled to an electrical stimulation generator. The programming device is adapted to be in communication with the electrical stimulation generator and a patient feedback device. The programming device includes, a first communication port for communication with the electrical stimulation generator, a second communication port for communication with the patient feedback device, a user interface; and a controller coupled to the first communication port, the second communication port, and the user interface. The controller is configured to create the protocol for providing electrical stimulation to treat the patient.

In another embodiment, the present disclosure provides a system for providing therapeutic electrical stimuli to a patient. The system includes one or more implantable medical leads having a plurality of electrodes, an electrical stimulation generator coupled to the lead, a patient feedback device, and a programming device in communication with the electrical stimulation generator and in communication with the patient feedback device. The programming device configured to initiate a first automated and systematic sweep through the plurality of electrodes to determine a respective perception threshold associated with each electrode, receive from the patient feedback device whether the patient provided feedback while performing the first automated and systematic sweep, initiate a second automated and systematic sweep through the plurality of electrodes to determine an electrode that is associated with a pain area of the patient, receive from the patient feedback device whether the patient provided feedback while performing the second automated and systematic sweep, and develop the protocol for providing therapeutic electrical stimulation to treat the patient based on the second automated and systematic sweep and the detected patient feedback. The second automated and systematic sweep uses the respective perception thresholds from the first automated and systematic sweep.

In another embodiment, the present disclosure provides a patient feedback device for providing feedback to a programming device of an electrical stimulation system providing therapeutic stimulation. The patient feedback device includes a sensor supported by the ergonomic housing. The sensor receives a physical response from the patient and provides an electrical signal in response thereto. The patient feedback device further includes a controller supported by the housing and coupled to the sensor and a communication port supported by the housing and coupled to the controller. The controller receives the electrical signal and initiates a communication signal in response thereto. The communication port receives the communication signal and transmits the communication signal to the programming device.

In another embodiment, the present disclosure provides an electronic device for performing a computer-assisted stimulation programming of an implantable medical device. The electronic device includes a memory storage component configured to store programming code. The electronic device also includes a computer processor configured to execute the programming code. When the programming code is executed, stimulation current is ramped up for a plurality of contacts on a lead that is configured to be implanted inside, or attached to, a patient. Patient feedback is received while the stimulation current is being ramped up. The patient feedback indicates that the patient is beginning to feel stimulation. In response to receiving the patient feedback: Amplitude of the stimulation current that resulted in the patient feedback is recorded. The plurality of contacts is divided into a plurality of groups. The contacts are activated one group at a time. The respective amplitudes of the stimulation currents of the contacts in each group are set to the recorded amplitude. For each activated group of contacts, it is determined whether the patient is able to feel stimulation while said group of contacts is being activated. In response to a determination that a target group of contacts causes the patient to feel stimulation, the target group of contacts are divided into a plurality of sub-groups. Thereafter, the dividing, the activating, the determining, and the sub-dividing are repeated one or more times until one or more contacts that caused the patient to feel stimulation are identified. The recorded amplitude is assigned as a perception threshold for the identified one or more contacts.

In another embodiment, the present disclosure provides a medical system. The medical system includes a lead configured to deliver electrical stimulation to a patient via one or more of a plurality of contacts located on the lead. The medical system includes a pulse generator to which the lead is coupled. The pulse generator is configured to generate the electrical stimulation. The medical system includes an electronic device coupled to the pulse generator. The electronic device is configured to program the pulse generator to generate the electrical stimulation. The electronic device includes a memory storage component configured to store programming code. The electronic device also includes a computer processor configured to execute the programming code. When the programming code is executed, stimulation current is ramped up for a plurality of contacts on a lead that is configured to be implanted inside, or attached to, a patient. Patient feedback is received while the stimulation current is being ramped up. The patient feedback indicates that the patient is beginning to feel stimulation. In response to receiving the patient feedback: Amplitude of the stimulation current that resulted in the patient feedback is recorded. The plurality of contacts is divided into a plurality of groups. The contacts are activated one group at a time. The respective amplitudes of the stimulation currents of the contacts in each group are set to the recorded amplitude. For each activated group of contacts, it is determined whether the patient is able to feel stimulation while said group of contacts is being activated. In response to a determination that a target group of contacts causes the patient to feel stimulation, the target group of contacts are divided into a plurality of sub-groups. Thereafter, the dividing, the activating, the determining, and the sub-dividing are repeated one or more times until one or more contacts that caused the patient to feel stimulation are identified. The recorded amplitude is assigned as a perception threshold for the identified one or more contacts.

In another embodiment, the present disclosure provides a method of performing a computer-assisted stimulation programming of an implantable medical device. A stimulation current is ramped up for a plurality of contacts on a lead that is configured to be implanted inside, or attached to, a patient. Patient feedback is received while the stimulation current is being ramped up. The patient feedback indicates that the patient is beginning to feel stimulation. In response to receiving the patient feedback: Amplitude of the stimulation current that resulted in the patient feedback is recorded. The plurality of contacts is divided into a plurality of groups. The contacts are activated one group at a time. The respective amplitudes of the stimulation currents of the contacts in each group are set to the recorded amplitude. For each activated group of contacts, it is determined whether the patient is able to feel stimulation while said group of contacts is being activated. In response to a determination that a target group of contacts causes the patient to feel stimulation, the target group of contacts are divided into a plurality of sub-groups. Thereafter, the dividing, the activating, the determining, and the sub-dividing are repeated one or more times until one or more contacts that caused the patient to feel stimulation are identified. The recorded amplitude is assigned as a perception threshold for the identified one or more contacts.

In another embodiment, the present disclosure involves an electronic device for performing a computer-assisted stimulation programming of an implantable medical device. The electronic device comprises: a memory storage component configured to store programming code; and a computer processor configured to execute the programming code to perform the following tasks: determining a non-zero starting value for ramping up a stimulation parameter for an electrical stimulation to be delivered to a patient, the non-zero starting value being customized to the patient; causing a pulse generator to generate the electrical stimulation to be delivered to the patient via a lead implanted inside the patient, wherein the causing the pulse generator to generate the electrical stimulation comprises causing the pulse generator to ramp up, from the determined non-zero starting value and toward a predefined maximum limit value, the stimulation parameter for a plurality of electrode contacts on the lead; receiving feedback from the patient in response to the ramping up of the stimulation parameter, the feedback being received at least in part via an electronic patient feedback device; and determining, based on the ramping up and the received feedback from the patient, a perception threshold for each of the plurality of electrode contacts, the perception threshold being a value of the stimulation parameter that corresponds to the patient feeling the electrical stimulation.

In another embodiment, the present disclosure involves a medical system. The medical system comprises: a lead configured to deliver electrical stimulation to a patient via one or more of a plurality of contacts located on the lead; a pulse generator to which the lead is coupled, wherein the pulse generator is configured to generate the electrical stimulation; and an electronic device telecommunicatively coupled to the pulse generator, wherein the electronic device is configured to program the pulse generator to generate the electrical stimulation, and wherein the electronic device includes: a memory storage component configured to store computer instructions; and a processor component configured to execute the computer instructions. The computer instructions, when executed by the processor component, perform the following tasks: determining a non-zero starting value for ramping up a stimulation parameter for an electrical stimulation to be delivered to a patient, the non-zero starting value being customized to the patient; causing a pulse generator to generate the electrical stimulation to be delivered to the patient via a lead implanted inside the patient, wherein the causing the pulse generator to generate the electrical stimulation comprises causing the pulse generator to ramp up, from the determined non-zero starting value and toward a predefined maximum limit value, the stimulation parameter for a plurality of electrode contacts on the lead; receiving feedback from the patient in response to the ramping up of the stimulation parameter; and determining, based on the ramping up and the received feedback from the patient, a perception threshold for each of the plurality of electrode contacts, the perception threshold being a value of the stimulation parameter that corresponds to the patient feeling the electrical stimulation.

In another embodiment, the present disclosure involves a method for performing a computer-assisted stimulation programming of an implantable medical device, comprising: determining a non-zero starting value for ramping up a stimulation parameter for an electrical stimulation to be delivered to a patient, the non-zero starting value being customized to the patient; causing a pulse generator to generate the electrical stimulation to be delivered to the patient via a lead implanted inside the patient, wherein the causing the pulse generator to generate the electrical stimulation comprises causing the pulse generator to ramp up, from the determined non-zero starting value and toward a predefined maximum limit value, the stimulation parameter for a plurality of electrode contacts on the lead; receiving feedback from the patient in response to the ramping up of the stimulation parameter, the feedback being received via an electronic patient feedback device; and determining, based on the ramping up and the received feedback from the patient, a perception threshold for each of the plurality of electrode contacts, the perception threshold being a value of the stimulation parameter that corresponds to the patient feeling the electrical stimulation.

Other aspects of the invention will become apparent by consideration of the detailed description and accompanying drawings.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

FIGS. 26-30 and 32 are example screenshots of a user interface 1200 for visually representing different aspects of the CASP and alternative CASP processes according to the various embodiments of the present disclosure.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The invention herein relates to an electrical stimulation system for providing stimulation to target tissue of a patient. The system described in detail below is a spinal cord stimulation (SCS) system for providing electrical pulses to the neurons of the spinal cord of a patient. However, many aspects of the invention are not limited to spinal cord stimulation. The electrical stimulation system may provide stimulation to other body portions including a muscle or muscle group, nerves, the brain, etc.

Figure 1:
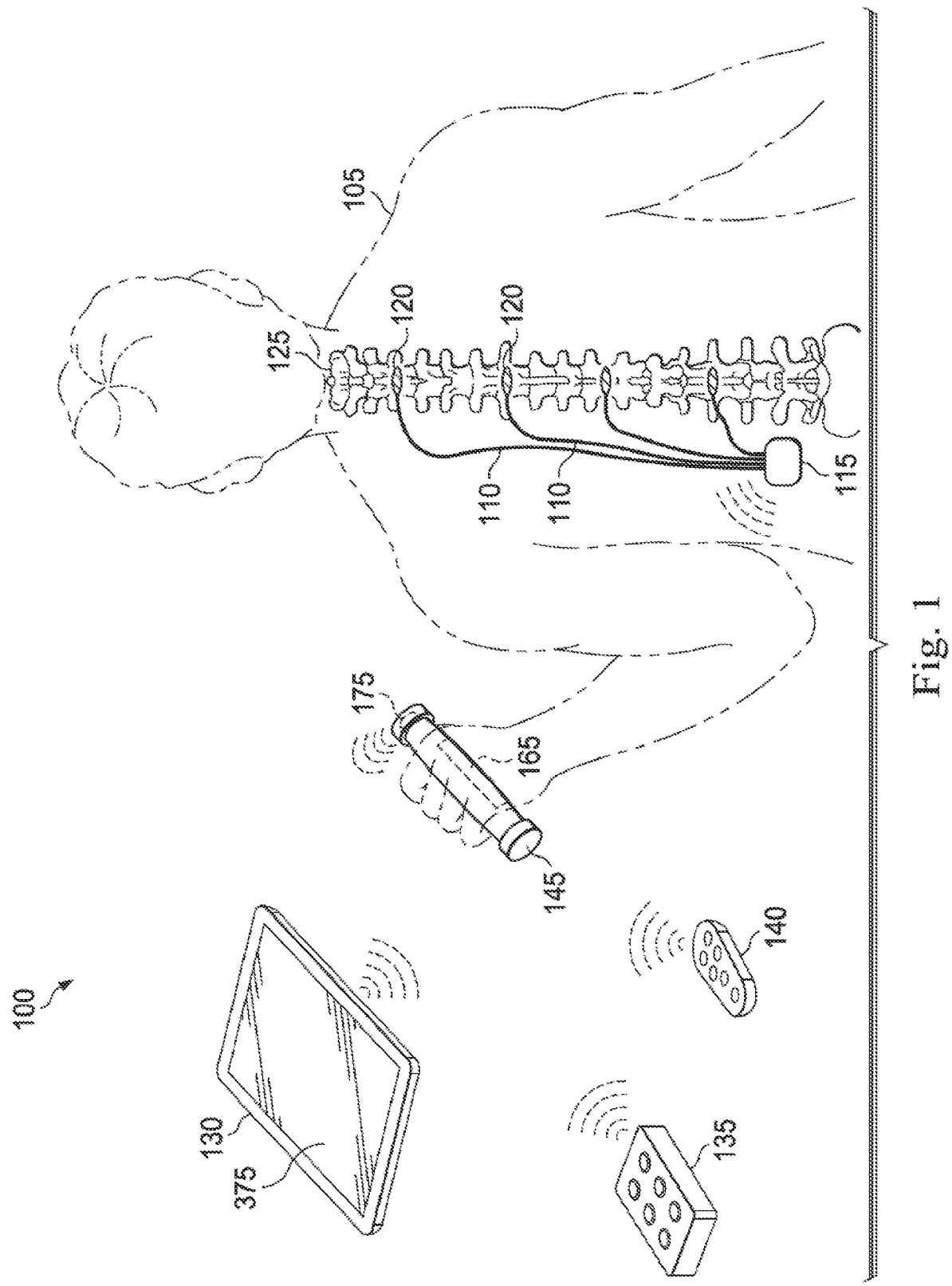
FIG. 1 is a partial perspective view of a patient using a spinal cord stimulation system.

FIG. 1 shows a spinal cord stimulation system 100 in use with a patient 105. The system includes one or more implanted medical electrical leads 110 connected to an implantable pulse generator (IPG) 115. The leads 110 include an electrode array 120 at a distal end of the base lead cable. The electrode array 120 includes one or more electrical stimulation electrodes (may also be referred as electrode contacts or simply electrodes) and is placed adjacent to the dura of the spine 125 using an anchor. The spinal column includes the C1-C7 (cervical), T1-T12 (thoracic), L1-L5 (lumbar) and S1-S6 (sacral) vertebrae and the electrode array(s) 120 may be positioned anywhere along the spine 125 to deliver the intended therapeutic effects of spinal cord electrical stimulation in a desired region of the spine. The electrodes (discussed further in FIGS. 2 and 3) of the electrode arrays 120 promote electrical stimulation to the neurons of the spine based on electrical signals generated by the IPG 115. In one construction, the electrical signals are regulated current pulses that are rectangular in shape. However, the electrical signals can be other types of signals, including other types of pulses (e.g., regulated voltage pulses), and other shapes of pulses (e.g., trapezoidal, sinusoidal). The stimulation is provided from the IPG 115 to the electrodes via the base lead, which is connected to the IPG 115 with the proximal end of the base lead. The body of the lead can traverse through the body of the patient via the spinal column and from the spinal column through the body of the patient to the implant site of the IPG 115.

The IPG 115 generates the electrical signals through a multiplicity of electrodes (e.g., four, eight, sixteen, twenty-four electrodes). The IPG 115 can control six aspects of electrical stimulation based on a protocol (may also be referred to as a program): on/off, amplitude (e.g., current or voltage), frequency, pulse width, pulse shape, and polarity (anodic or cathodic stimulation). The stimulation most discussed herein is a regulated (or constant) current that provides a square wave, cathodic stimulation with a variable amplitude, frequency, and/or pulse width. Typically, the IPG 115 is implanted in a surgically made pocket (e.g., in the abdomen) of the patient. However, the pulse generator can also be an external pulse generator (EPG).

The IPG 115 communicates with any one of a clinician programmer (CP) 130, a patient programmer and charger (PPC) 135, and a pocket (or fob) programmer (PP) 140. As discussed in further detail below, the CP 130 interacts with the IPG 115 to develop a protocol for stimulating the patient. The developing of the protocol is assisted with the use of a patient-feedback device (PFD) 145. Once a protocol is developed, the PPC 135 or the PP 140 can activate, deactivate, or perform limited changes to the programming parameters of the protocol. The protocol may be stored at the IPG 115 or can be communicated and stored at the PPC 135 or the PP 140. The PPC 135 is also used for charging the IPG 115.

For the construction described herein, the IPG 115 includes a rechargeable, multichannel, radio-frequency (RF) programmable pulse generator housed in a metallic (e.g., titanium) case or housing. The metallic case is sometimes referred to as the "can" and may act either as a cathode or an anode or floating to the electrical contacts.

Figure 3:
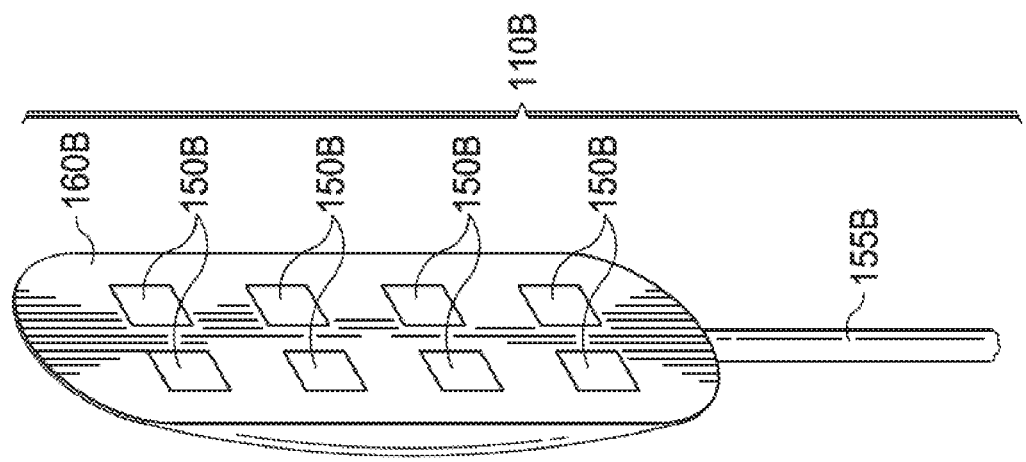
FIG. 3 is a perspective view of a paddle lead for use in the spinal cord stimulation system of FIG. 1.
Figure 2:
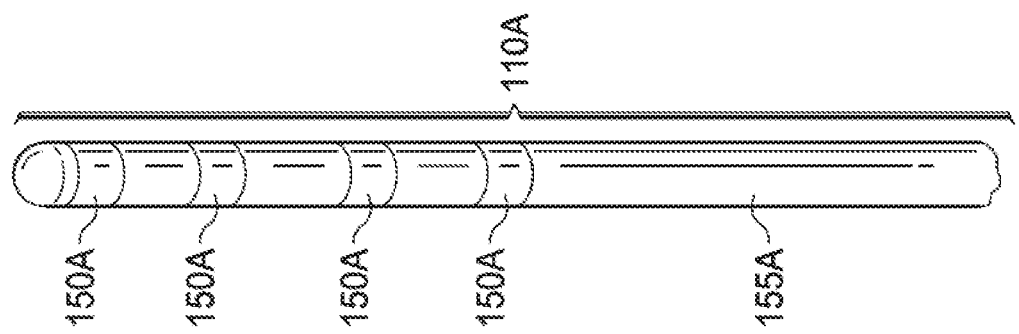
FIG. 2 is a perspective view of an in-line lead for use in the spinal cord stimulation system of FIG. 1.

Referring now to FIGS. 2 and 3, the figures show two exemplary leads 110A and 110B, respectively, that can be used in the SCS system. A first common type of lead 110 is the "in-line" lead shown in FIG. 2. An in-line lead 110A includes individual electrodes 150A along the length of a flexible cable 155A. A second common type of lead 110 is the "paddle" lead shown in FIG. 3. In general, the paddle lead 110B is shaped with a wide platform 160B on which a variety of electrode 150B configurations are situated. For example, the paddle lead 110B shown in FIG. 3 has two columns of four rectangular shaped electrodes 150B. A paddle lead typically contains contacts on one side only, but is not restricted to individual electrodes on either side, or electrodes perforating the carrier material.

For both leads shown in FIGS. 2 and 3, a flexible cable 155A or 155B has respective small wires for the electrodes 150A or 150B. The wires are embedded within the cable 155A or 155B and carry the electrical stimulation from the IPG 115 to the electrodes 150A or 150B.

It is envisioned that other types of leads 110 and electrode arrays 120 can be used with the invention. Also, the number of electrodes 150 and how the electrodes 150 are arranged in the electrode array 120 can vary from the examples discussed herein.

The leads shown in FIGS. 2 and 3 are multiple channel leads. Here, a "channel" is defined as a specified electrode 150, or group of electrodes 150, that receives a specified pattern or sequence of electrical stimuli. For simplicity, this description will focus on each electrode 150 and the IPG's 115 metallic housing providing a respective channel. When more than one channel is available, each channel may be programmed to provide its own stimulus to its defined electrode.

There are many instances when it is advantageous to have multiple channels for stimulation. For example, different pain locations (e.g., upper extremities, lower extremities) of the patient may require different stimuli. Further, some patients may exhibit conditions better suited to "horizontal" stimulation paths, while other patients may exhibit conditions better suited to "vertical" stimulation paths. Therefore, multiple electrodes positioned to provide multiple channels can cover more tissue/neuron area, and thereby provide better stimulation protocol flexibility to treat the patient.

It is also envisioned that the number of leads 110 can vary. For example, one, two, or four leads 110 can be connected to the IPG 115. The electrode arrays 120 of the leads 110, respectively, can be disposed in different vertical locations on the spine 125 with respect to a vertical patient 105, can be disposed horizontally (or "side-by-side") on the spine 125 with respect to a vertical patient 105, or some combination thereof.

In alternative to the IPG 115, the leads 110 can receive electrical stimuli from an external pulse generator (EPG) (also referred to a trial stimulator) through one or more percutaneous lead extensions. An EPG may be used during a trial period.

For the specific construction and operation described herein, a single lead 110 having a two-by-four electrode paddle (as shown in FIG. 3) is secured to the thoracic portion of the spine 125. An IPG 115 having a metallic housing is disposed within the patient 105. The housing acts as another electrode in this contemplated SCS system 100. Thus, this arrangement results in nine electrodes total. Also, the specifically-discussed system includes nine channels formed by the eight electrodes of the electrode array 120, respectively, and the metallic housing of the IPG 115. However, it contemplated that a different number of leads, electrodes, and channels fall within the scope of the invention.

Referring back to FIG. 1, a user provides feedback to the CP 130 with a PFD 145 while the CP 130 develops the protocol for the IPG 115. In FIG. 1, the PFD 145 is an ergonomic handheld device having a sensor (also referred to as input) 165, a controller, and a communications output 175. The sensor 165 can take the form of a discrete switch or can take the form of a continuously variable input, such as through the use of a strain gauge. It is envisioned that the use of a continuously variable input can provide magnitude information, thereby providing feedback information.

Figure 4:
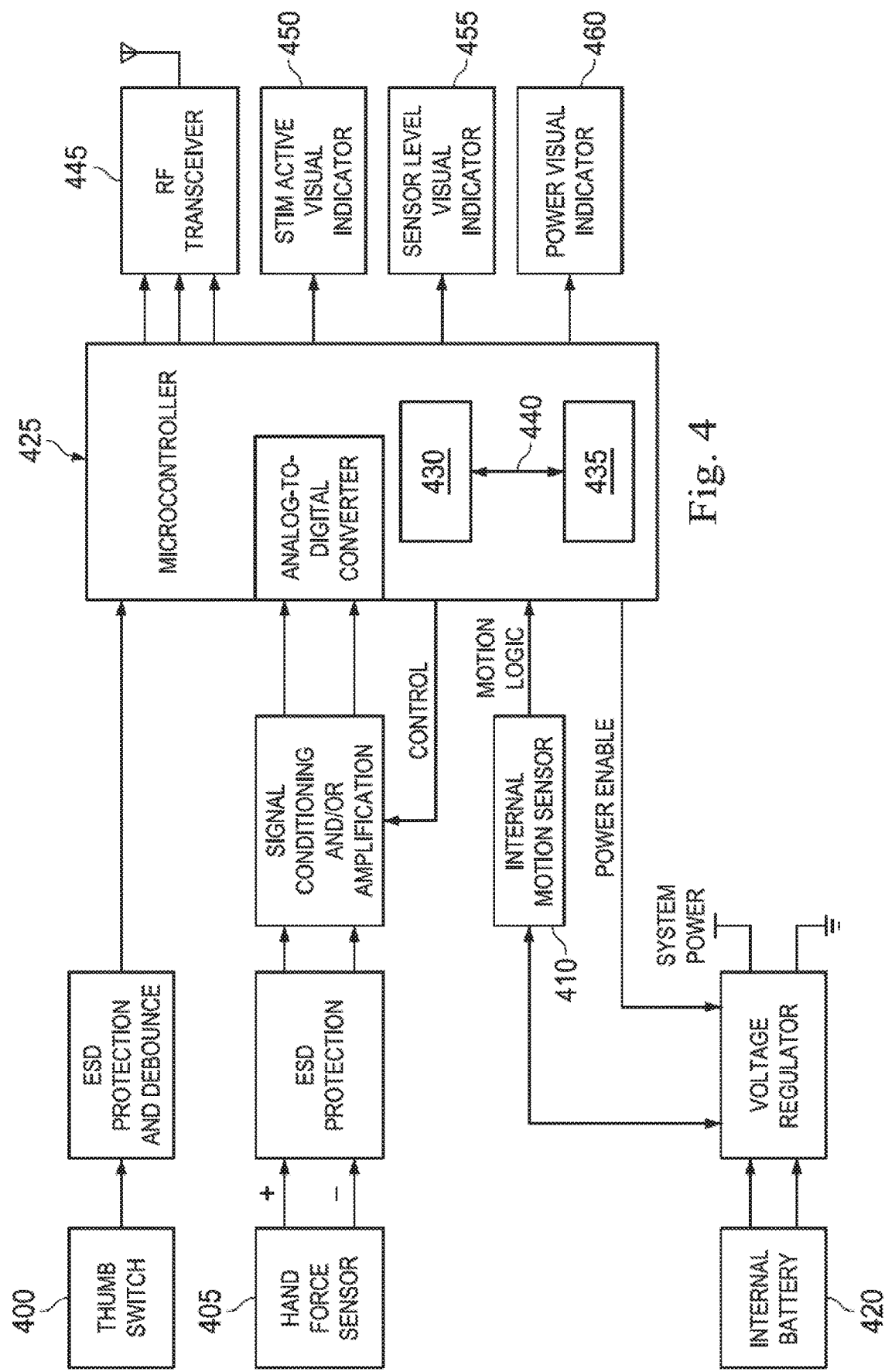
FIG. 4 is a block diagram of a patient-feedback device for use in the spinal cord stimulation system of FIG. 1.

FIG. 4 provides a block diagram of an exemplary handheld PFD 145 used in the SCS system 100. The PFD 145 includes two inputs 900 and 905 in communication with the housing of the device 145 and one input 910 internal to the housing. One of the external inputs 900 is a binary ON/OFF switch, preferably activated by the patient's thumb, to allow the patient 105 to immediately deactivate stimulation. The second input 905 includes a force or displacement sensor sensing the pressure or force exerted by the patient's hand. The sensed parameter can be either isotonic (constant force, measuring the distance traversed) or isometric (measuring the force, proportional to pressure applied by patient 105). The resulting signal from the sensor 905 is analog and, therefore, the signal is conditioned, amplified, and passed to a microcontroller via an analog-to-digital converter.

The internal input 910 for the PFD 145 of FIG. 4 is a motion sensor. The sensor 910, upon detecting motion, initiates activation of the PFD 145. The device 145 stays active until movement is not detected by the sensor 910 for a time period. Power is provided by an internal battery 920 that can be replaceable and/or rechargeable.

The processing of the inputs from the sensors 900 and 905 take place in a controller, such as a microcontroller 925. The microcontroller 925 includes a suitable programmable portion 930 (e.g., a microprocessor or a digital signal processor), a memory 935, and a bus 940 or other communication lines. Output data of the microcontroller 925 is sent via a Bluetooth bi-direction radio communication portion 945 to the CP 130. The Bluetooth portion 945 includes a Bluetooth communication interface, an antenna switch, and a related antenna, all of which allows wireless communication following the Bluetooth Special Interest Group standard. Other outputs may include indicators (such as light-emitting diodes) for communicating stimulation activity 950, sensor activation 955, and device power 960, and a speaker and related circuitry 965 for audible communication.

As discussed further below, the patient 105 provides feedback to the SCS system 100, and specifically the CP 130, while the CP 130 establishes the protocol for the IPG 115. The patient 105 can activate the PFD 145 when the patient 105 feels various stimuli, such as paresthesia or pain. Paresthesia refers to a comfortable tingly or buzzing sensation that masks the pain.

Figure 6:
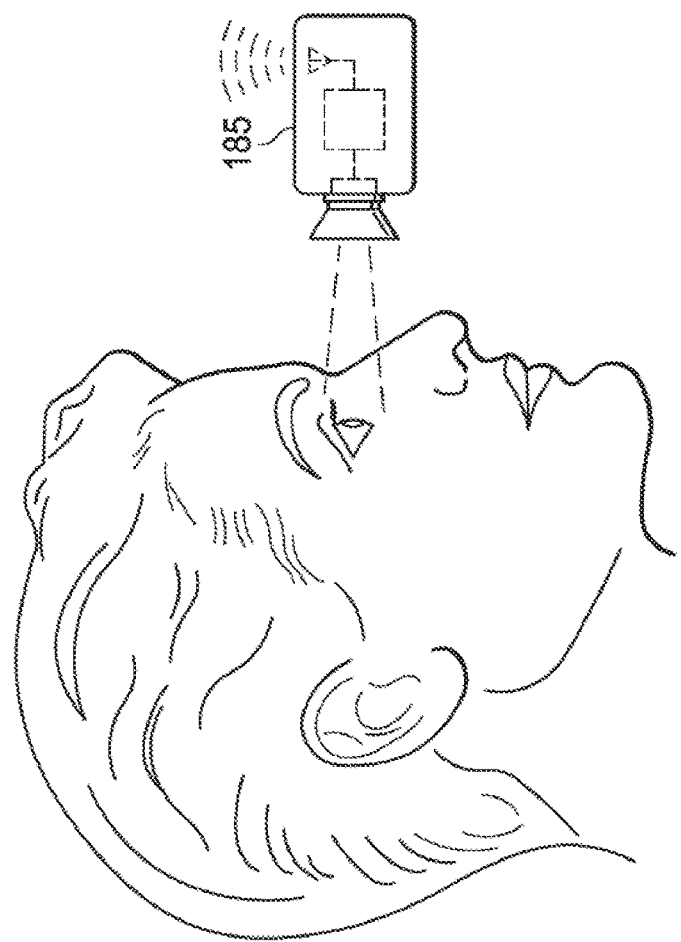
FIG. 6 is a side view of a patient-feedback device with optical sensing.
Figure 5:
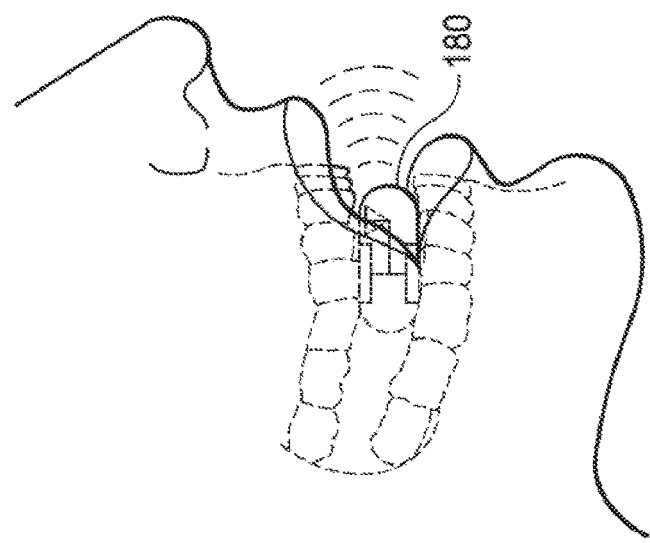
FIG. 5 is a side view of a patient-feedback device inserted in the mouth of a patient
Figure 7:
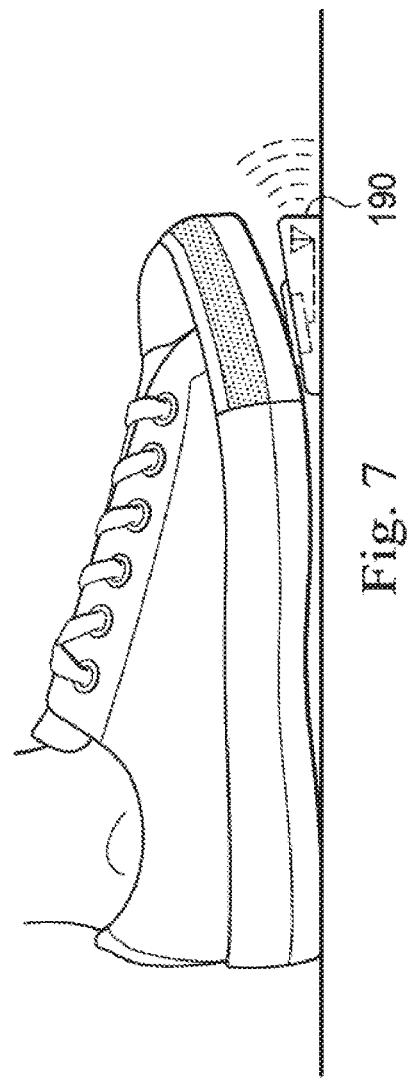
FIG. 7 is a side view of a patient-feedback device activated by a foot of a patient.

FIGS. 5-7 provide other means for receiving patient feedback. More specifically, FIG. 5 shows a mouth-piece 180 that is inserted into the mouth of the patient. The user provides feedback by biting the mouthpiece. FIG. 6 shows an optical sensor 185 (such as a camera and related image processing software) that detects visual cues from a patient. An example visual cue may be the blinking of the patient's eyes. FIG. 7 shows a foot pedal 190 that receives input by the patient manipulating a switch with his foot. It is also envisioned that the patient may provide feedback directly through the touch screen or hard buttons on the CP 130.

As discussed earlier, it should be understood that aspects of the SCS system 110 can be applied to other types of electrical stimulation systems. That is, other electrical stimulation systems provide electrical stimuli to other types of target tissues. Similar to the SCS system 110, these other electrical stimulation systems include one or more medical electrical leads having electrodes, a stimulation generator coupled to the one or more medical electrical leads, and a clinician programmer for establishing a protocol with the stimulation generator.

Figure 8:
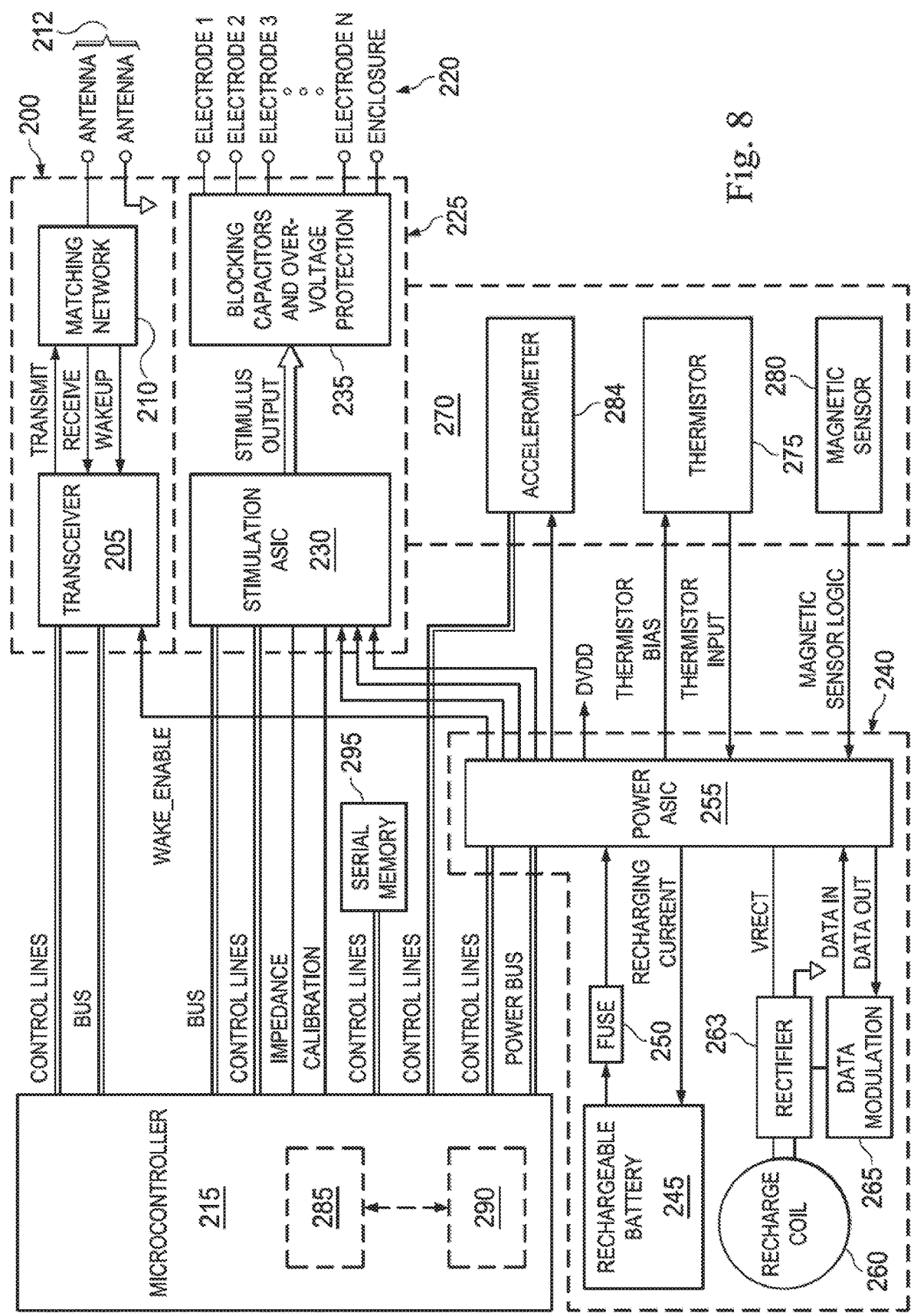
FIG. 8 is a block diagram of an implantable pulse generator for use in the spinal cord stimulation system of FIG. 1.

FIG. 8 shows a block diagram of one construction of the IPG 115. The IPG 115 includes a printed circuit board ("PCB") that is populated with a plurality of electrical and electronic components that provide power, operational control, and protection to the IPG 115. With reference to FIG. 8, the IPG 115 includes a communication portion 200 having a transceiver 205, a matching network 210, and antenna 212. The communication portion 200 receives power from a power ASIC (discussed below), and communicates information to/from the microcontroller 215 and a device (e.g., the CP 130) external to the IPG 115. For example, the IPG 115 can provide bi-direction radio communication capabilities, including Medical Implant Communication Service (MICS) bi-direction radio communication following the MICS specification.

The IPG 115, as previously discussed, provides stimuli to electrodes 150 of an implanted medical electrical lead 110. As shown in FIG. 8, N electrodes 150 are connected to the IPG 115. In addition, the enclosure or housing 220 of the IPG 115 can act as an electrode. The stimuli are provided by a stimulation portion 225 in response to commands from the microcontroller 215. The stimulation portion 225 includes a stimulation application specific integrated circuit (ASIC) 230 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, Flash, etc. The stimulation ASIC 230 can include a processor, memory, and firmware for storing preset pulses and protocols that can be selected via the microcontroller 215. The providing of the pulses to the electrodes 150 is controlled through the use of a waveform generator and amplitude multiplier of the stimulation ASIC 230, and the blocking capacitors and overvoltage protection circuitry of the stimulation portion 225, as is known in the art. The stimulation portion 225 of the IPG 115 receives power from the power ASIC (discussed below). The stimulation ASIC 230 also provides signals to the microcontroller 215. More specifically, the stimulation ASIC 230 can provide impedance values for the channels associated with the electrodes 150, and also communicate calibration information with the microcontroller 215 during calibration of the IPG 115.

The IPG 115 also includes a power supply portion 240. The power supply portion includes a rechargeable battery 245, fuse 250, power ASIC 255, recharge coil 260, rectifier 263 and data modulation circuit 265. The rechargeable battery 245 provides a power source for the power supply portion 240. The recharge coil 260 receives a wireless signal from the PPC 135. The wireless signal includes an energy that is converted and conditioned to a power signal by the rectifier 263. The power signal is provided to the rechargeable battery 245 via the power ASIC 255. The power ASIC 255 manages the power for the IPG 115. The power ASIC 255 provides one or more voltages to the other electrical and electronic circuits of the IPG 155. The data modulation circuit 265 controls the charging process.

The IPG also includes a section 270 that includes a thermistor 275, a magnetic sensor 280, and an accelerometer 284. The thermistor 275 senses a temperature. The magnetic sensor 280 provides a "hard" switch upon sensing a magnet for a defined period. The signal from the magnetic sensor 280 can provide an override for the IPG 115 if a fault is occurring with the IPG 115 and is not responding to other controllers. The accelerometer 284 senses movement or acceleration of the IPG.

The IPG 115 is shown in FIG. 8 as having a microcontroller 215. Generally speaking, the microcontroller 215 is a controller for controlling the IPG 115. The microcontroller 215 includes a suitable programmable portion 285 (e.g., a microprocessor or a digital signal processor), a memory 290, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at www.ti.com; the content of the data sheet being incorporated herein by reference.

The IPG 115 includes memory, which can be internal to the control device (such as memory 290), external to the control device (such as serial memory 295), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 285 executes software that is capable of being stored in the RAM (e.g., during execution), the ROM (e.g., on a generally permanent basis), or another non-transitory computer readable medium such as another memory or a disc.

Software included in the implementation of the IPG 115 is stored in the memory 290. The software includes, for example, firmware, one or more applications, program data, one or more program modules, and other executable instructions. The programmable portion 285 is configured to retrieve from memory and execute, among other things, instructions related to the control processes and methods described below for the IPG 115. For example, the programmable portion 285 is configured to execute instructions retrieved from the memory 290 for sweeping the electrodes 150 in response to a signal from the CP 130.

The PCB also includes a plurality of additional passive and active components such as resistors, capacitors, inductors, integrated circuits, and amplifiers. These components are arranged and connected to provide a plurality of electrical functions to the PCB including, among other things, filtering, signal conditioning, or voltage regulation, as is commonly known.

Figure 9:
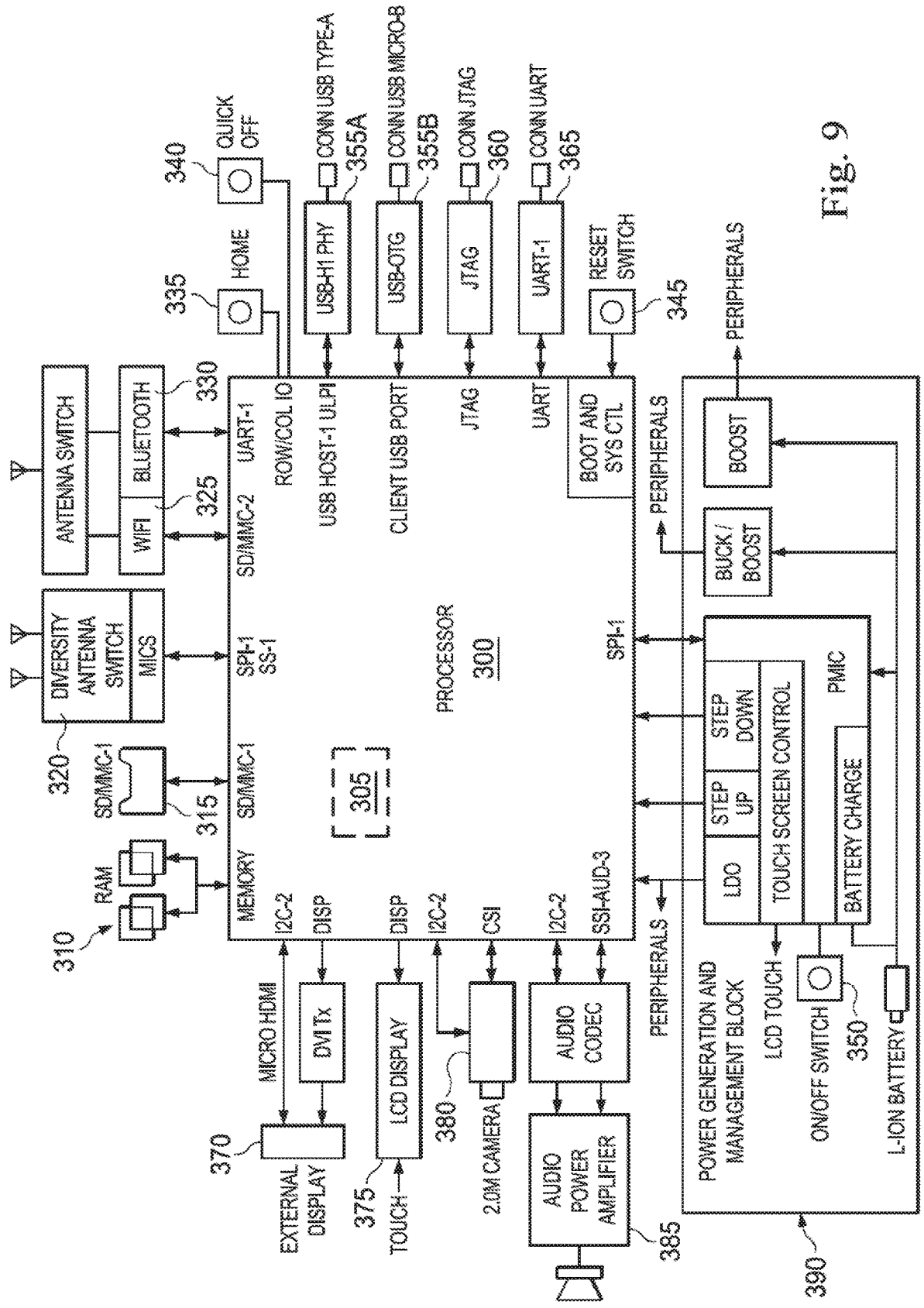
FIG. 9 is a block diagram of a clinician programmer for use in the spinal cord stimulation system of FIG. 1.

FIG. 9 shows a block diagram of one construction of the CP 130. The CP 130 includes a printed circuit board ("PCB") that is populated with a plurality of electrical and electronic components that provide power, operational control, and protection to the CP 130. With reference to FIG. 9, the CP includes a processor 300. The processor 300 is a controller for controlling the CP 130 and, indirectly, the IPG 115 as discussed further below. In one construction, the processor 300 is an applications processor model i.MX515 available from Freescale Semiconductor. More specifically, the i.MX515 applications processor has internal instruction and data cashes, multimedia capabilities, external memory interfacing, and interfacing flexibility. Further information regarding the i.MX515 applications processor can be found in, for example, the "IMX510EC, Rev. 4" data sheet; dated August 2010; published by Freescale Semiconductor at www.freescale.com, the content of the data sheet being incorporated herein by reference. Of course, other processing units, such as other microprocessors, microcontrollers, digital signal processors, etc., can be used in place of the processor 300.

The CP 130 includes memory, which can be internal to the processor 300 (e.g., memory 305), external to the processor 300 (e.g., memory 310), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 300 executes software that is capable of being stored in the RAM (e.g., during execution), the ROM (e.g., on a generally permanent basis), or another non-transitory computer readable medium such as another memory or a disc. The CP 130 also includes input/output ("I/O") systems that include routines for transferring information between components within the processor 300 and other components of the CP 130 or external to the CP 130.

Software included in the implementation of the CP 130 is stored in the memory 305 of the processor 300, RAM 310, ROM 315, or external to the CP 130. The software includes, for example, firmware, one or more applications, program data, one or more program modules, and other executable instructions. The processor 300 is configured to retrieve from memory and execute, among other things, instructions related to the control processes and methods described below for the CP 130. For example, the processor 300 is configured to execute instructions retrieved from the memory 140 for establishing a protocol to control the IPG 115.

One memory shown in FIG. 9 is memory 310, which can be a double data rate (DDR2) synchronous dynamic random access memory (SDRAM) for storing data relating to and captured during the operation of the CP 130. In addition, a secure digital (SD) multimedia card (MMC) can be coupled to the CP for transferring data from the CP to the memory card via slot 315. Of course, other types of data storage devices can be used in place of the data storage devices shown in FIG. 9.

The CP 130 includes multiple bi-directional radio communication capabilities. Specific wireless portions included with the CP 130 are a Medical Implant Communication Service (MICS) bi-direction radio communication portion 320, a WiFi bi-direction radio communication portion 325, and a Bluetooth bi-direction radio communication portion 330. The MICS portion 320 includes a MICS communication interface, an antenna switch, and a related antenna, all of which allows wireless communication using the MICS specification. The WiFi portion 375 and Bluetooth portion 330 include a WiFi communication interface, a Bluetooth communication interface, an antenna switch, and a related antenna all of which allows wireless communication following the WiFi Alliance standard and Bluetooth Special Interest Group standard. Of course, other wireless local area network (WLAN) standards and wireless personal area networks (WPAN) standards can be used with the CP 130.

The CP 130 includes three hard buttons: a "home" button 335 for returning the CP to a home screen for the device, a "quick off" button 340 for quickly deactivating stimulation IPG, and a "reset" button 345 for rebooting the CP 130. The CP 130 also includes an "ON/OFF" switch 350, which is part of the power generation and management block (discussed below).

The CP 130 includes multiple communication portions for wired communication. Exemplary circuitry and ports for receiving a wired connector include a portion and related port for supporting universal serial bus (USB) connectivity 355, including a Type-A port and a Micro-B port; a portion and related port for supporting Joint Test Action Group (JTAG) connectivity 360, and a portion and related port for supporting universal asynchronous receiver/transmitter (UART) connectivity 365. Of course, other wired communication standards and connectivity can be used with or in place of the types shown in FIG. 9.

Another device connectable to the CP 130, and therefore supported by the CP 130, is an external display. The connection to the external display can be made via a micro High-Definition Multimedia Interface (HDMI) 370, which provides a compact audio/video interface for transmitting uncompressed digital data to the external display. The use of the HDMI connection 370 allows the CP 130 to transmit video (and audio) communication to an external display. This may be beneficial in situations where others (e.g., the surgeon) may want to view the information being viewed by the healthcare professional. The surgeon typically has no visual access to the CP 130 in the operating room unless an external screen is provided. The HDMI connection 370 allows the surgeon to view information from the CP 130, thereby allowing greater communication between the clinician and the surgeon. For a specific example, the HDMI connection 370 can broadcast a high definition television signal that allows the surgeon to view the same information that is shown on the LCD (discussed below) of the CP 130.

The CP 130 includes a touch screen I/O device 375 for providing a user interface with the clinician. The touch screen display 375 can be a liquid crystal display (LCD) having a resistive, capacitive, or similar touch-screen technology. It is envisioned that multitouch capabilities can be used with the touch screen display 375 depending on the type of technology used.

The CP 130 includes a camera 380 allowing the device to take pictures or video. The resulting image files can be used to document a procedure or an aspect of the procedure. For example, the camera 380 can be used to take pictures of barcodes associated with the IPG 115 or the leads 120, or documenting an aspect of the procedure, such as the positioning of the leads. Similarly, it is envisioned that the CP 130 can communicate with a fluoroscope or similar device to provide further documentation of the procedure. Other devices can be coupled to the CP 130 to provide further information, such as scanners or RFID detection. Similarly, the CP 130 includes an audio portion 385 having an audio codec circuit, audio power amplifier, and related speaker for providing audio communication to the user, such as the clinician or the surgeon.

The CP 130 further includes a power generation and management block 390. The power block 390 has a power source (e.g., a lithium-ion battery) and a power supply for providing multiple power voltages to the processor, LCD touch screen, and peripherals.

As best shown in FIG. 1, the CP 130 is a handheld computing tablet with touch screen capabilities. The tablet is a portable personal computer with a touch screen, which is typically the primary input device. However, an external keyboard or mouse can be attached to the CP 130. The tablet allows for mobile functionality not associated with even typical laptop personal computers.

In operation, the IPG 115 (which may also be an EPG) through the use of the implanted medical electrical leads 110, and specifically the electrodes 150, stimulates neurons of the spinal cord 125. The IPG 115 selects an electrode stimulating configuration, selects a stimulation waveform, regulates the amplitude of the electrical stimulation, controls the width and frequency of electrical pulses, and selects cathodic or anodic stimulation. This is accomplished by a healthcare professional (e.g., a clinician), using the CP 130, setting the parameters of the IPG 115. The setting of parameters of the IPG results in a "program," which is also referred to herein as a "protocol," for the electrode stimulation. Programming may result in multiple protocols that the patient can choose from. Multiple protocols allows, for example, the patient to find a best setting for paresthesia at a particular time of treatment.

With reference to FIG. 3, an electrode array 120 includes eight electrodes 150B. The shown electrode array 120 has two columns and four rows as viewed along a longitude length of the lead 110. More generically, the lead includes cl columns and r rows, where cl is two and r is four. When referring to a particular column, the column is referred to herein as the j-th column, and when referring to a particular row, the row is referred to as the i-th row.

Before proceeding further, it should be understood that not all electrode arrays 120 are conveniently shaped as a simple matrix having definite columns and definite rows. More complex configurations are possible, which are referred to herein as complex electrode array configurations. The processes discussed herein can account for complex electrode array configurations. For example, a representative array having cl columns and r rows for a complex electrode array configuration may include "dummy" addresses having "null" values in the array. For a specific example, an electrode contact may span multiple columns. The resulting array may have a first address i, j representing the multiple column electrode and a second address i, j+1 having a "null" value to account for the multiple columns of the multiple column electrode. This concept can be expanded to even more complex arrangements. Accordingly, all electrode arrays 120 can be addressed as a matrix and it will be assumed herein that the electrode array 120 has been addressed as a matrix.

One process of selecting a best protocol for providing electrical stimulation includes four sub-processes. The processes are referred to herein as the impedance sweep of electrodes, the perception-threshold sweep, the pain-coverage sweep, and the parameter fine adjustment. The selecting of a best protocol occurs during a method of treating a patient with spinal cord stimulation. FIGS. 10-15 provide multiple flow diagrams relating to the treatment of the patient 105 using the SCS 100.

Before proceeding further, it should be understood that the steps discussed in connection with FIGS. 10-15 will be discussed in an iterative manner for descriptive purposes. Various steps described herein with respect to the process of FIGS. 10-15 are capable of being executed in an order that differs from the illustrated serial and iterative manner of discussion. It is also envisioned that not all steps are required as described below.

Figure 10:
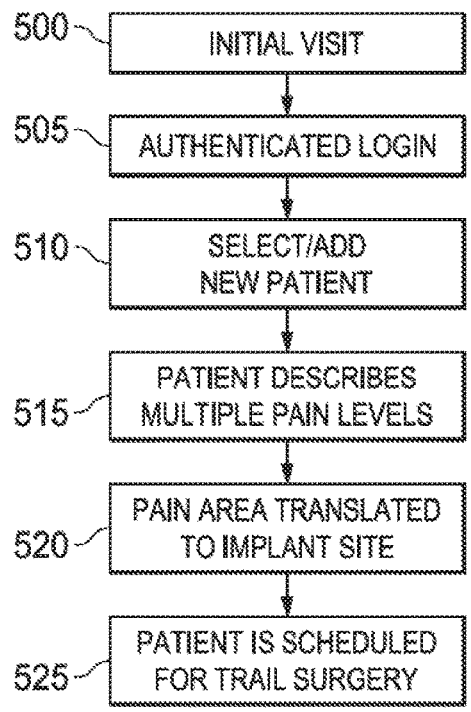
FIG. 10 is a flow diagram of a patient performing an initial visit with a clinician.

With reference to FIG. 10, the patient 105 performs an initial visit (block 500). The clinician working with the patient 105 logs into the CP 130 (block 505), and either selects a stored existing patient or adds a new patient to the CP 130 (block 510). The patient 105 then describes his pain area (block 515). Using the patient's description, implant sites for a future surgery (block 520) are determined. The patient 105 is then scheduled for trial surgery (block 525).

Figure 11:
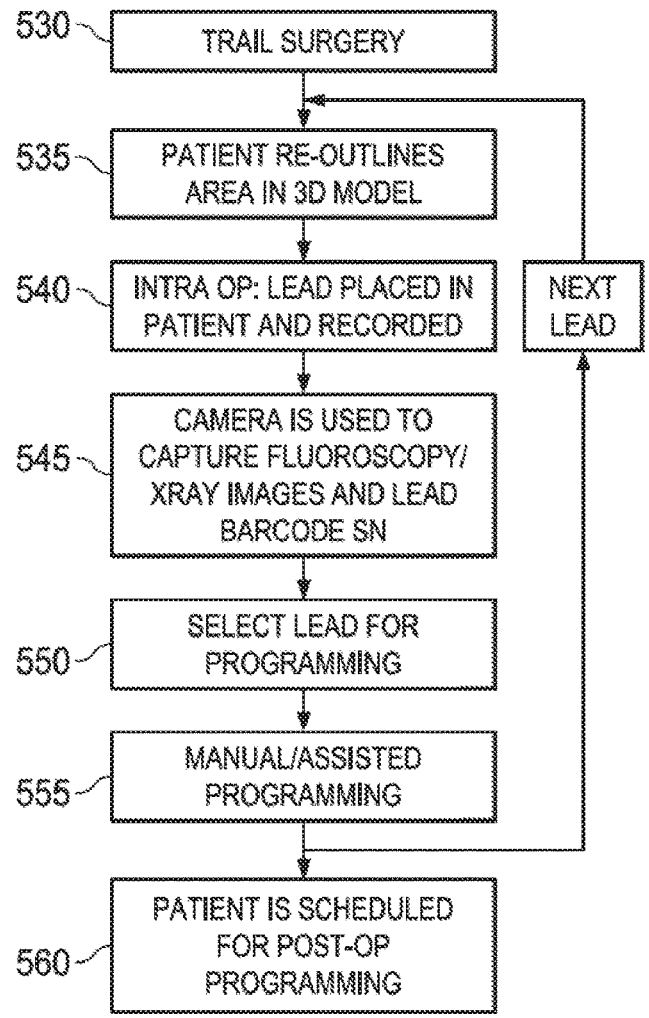
FIG. 11 is a flow diagram of a patient undergoing an initial visit followed by trial surgery procedure.
Figure 12:
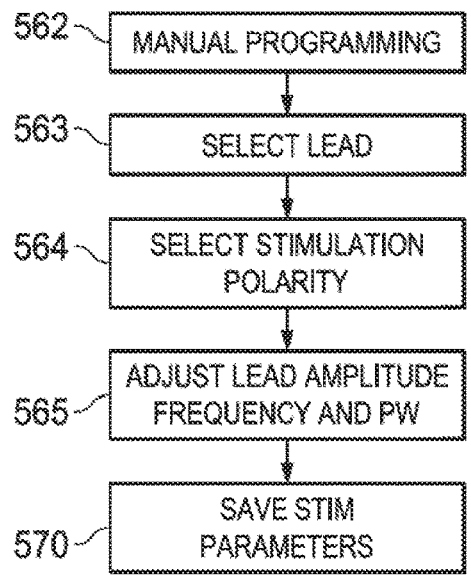
FIG. 12 is a flow diagram of the manual programming of a lead.
Figure 13:
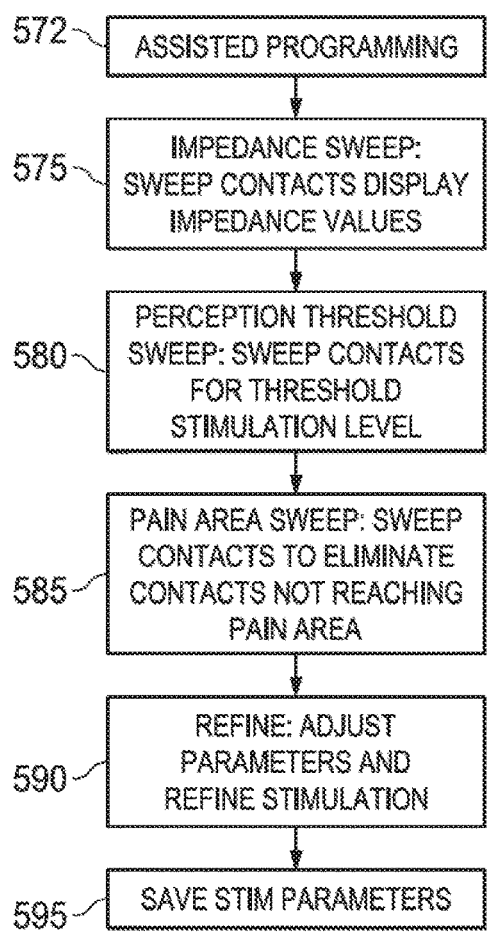
FIG. 13 is a flow diagram of the computer assisted programming of a lead.

Referring now to FIG. 11, the patient 105 returns for trial surgery (block 530). After obtaining the previously stored patient information, the patient 105 again describes his pain area (block 535) and the location for lead implant sites can be confirmed. During the procedure, one or more leads 110 are placed in the patient 105 and their respective locations recorded in the CP 130 (block 540). Further, the camera 380 can be used to capture images of the procedure, and capture/read barcode serial numbers of the leads 110 (block 545). It also envisioned that fluoroscopy/X-ray images can be recorded in the CP 130 as part of the procedure. The result of blocks 540 and 545 is that the CP 130 has a type, location, orientation, and other contextual information relating to the implanting of the lead 110. This provides a more robust and accurate programming of the lead 110.

Next (block 550), the clinician selects the lead 121 for programming. The programming can be manual or assisted (block 555), both of which are discussed below. The process can then be repeated for a next lead, or the patient is then scheduled for post-op programming (block 560).

Referring again to block 555, the clinician either manually or automatically programs the operation of the IPG 115 (which may also be an EPG) to provide electrical stimulation through the lead 110. With manual programming (FIG. 12, block 562), the clinician selects a lead (block 563), selects a stimulation polarity, which may be cathodal stimulation as it requires the least amount of current (voltage) to elicit a response (block 564), and manually adjusts pulse amplitude, frequency, and width of the electrical stimuli provided by the electrodes 150 (block 565). The patient 105 typically provides verbal responses to cues given by the clinician. This in particular is difficult and time consuming during a permanent implant where the patient has to be woken up from the general anesthesia and struggling to be cognitive with often speech impediments. This process can be very time consuming given the number of variables for each electrode/channel. The manual process also does not often result in a "best fit" for providing electrical stimulation treatment and relies significantly on the clinician's experience. The CP 130 saves the resulting protocol of the manually assisted programming (block 570).

With assisted programming (FIG. 13, block 572), the CP 130 establishes a protocol for providing electrical stimuli to the patient 105. More specifically, the assisted programming first performs three sweeps of the electrodes 150 to result in a best selection of the electrodes 150 for providing paresthesia. The first sweep (block 575) is an impedance sweep to determine a respective impedance between the IPG 115, connected lead, each electrode 150, and tissue. The impedances are displayed on the touch screen 375 and can be used by the clinician to help determine whether an electrode 150 falls in between an accepted impedance range. The second sweep (block 580) is a perception-threshold sweep to find the minimum threshold stimulation sensed by the patient 105 for each channel/electrode 150. The second sweep (block 580) is a perception-threshold sweep to find the minimum threshold. In one implementation, the stimulation sensed by the patient 105 for each channel/electrode 150 is cathodal polarity with the IPG 115 can being the anode. For an EPG, a reference electrode may represent the cathodal anode. The values of the perception-threshold sweep are used to normalize the initial sensation felt by the patient with each electrode 150. The last sweep (block 585) is a pain-area sweep to identify the optimal paresthesia electrodes to the pain area. Even more accurately, the pain-area sweep (block 585) eliminates contacts not reaching the pain area. The clinician can then repeat any of the sweeps and/or refine the paresthesia to the patient (block 590). The refining of the paresthesia can include adjusting parameters of electric stimulation through the electrodes identified in block 585, surrounding an electrode identified in block 585 with anode or cathode blocks, or shifting a pattern longitudinally or laterally, as is known in the art. After completion, the CP 130 saves the stimulation parameters (block 595). Further discussion regarding the CP 130 assisted programming will be provided below.

Before proceeding further, it should be noted that the contextual information relating to the implanting of the lead 110 (from blocks 540 and 545, above) can be used when programming the stimulation generator. That is, the contextual information can be used to exactly identify the lead 110, corresponding electrode array 120, orientation of the lead 110, the placement of the lead 110, etc. The CP 130 automatically accounts for this information when establishing the protocol. For a specific example, the CP allows for an anatomically correct placement of the stimulation lead, if the surgeon chooses to orient the lead in another way, such as antegrate or diagonal. The CP 130 accounts for this placement while performing the sweeps.

Figure 14:
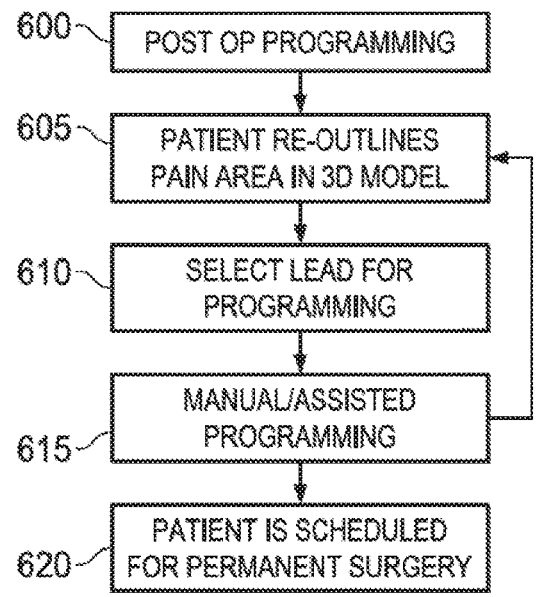
FIG. 14 is a flow diagram of a patient performing a post trial programming session.
Figure 15:
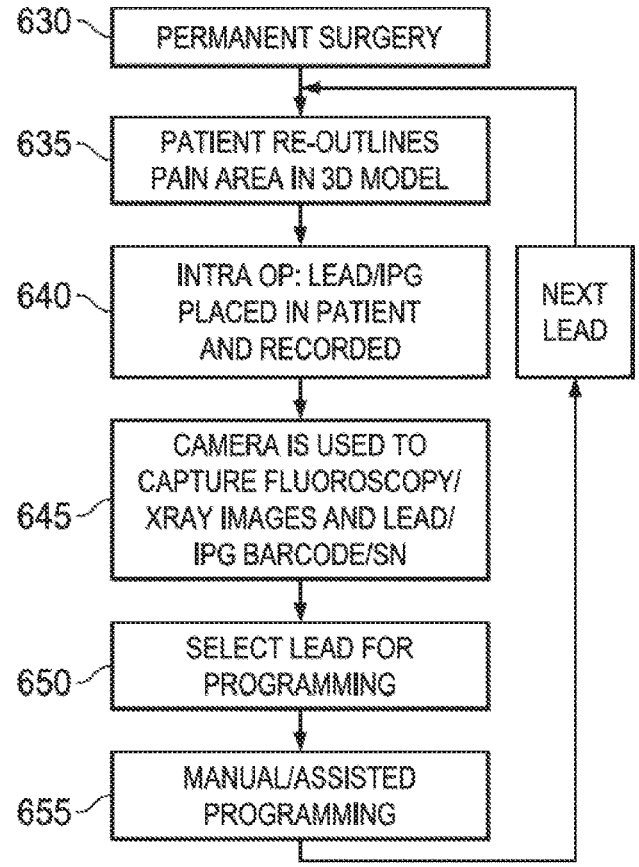
FIG. 15 is a flow diagram of a patient undergoing a permanent surgery procedure.

Referring now to FIG. 14, the patient 105 returns for post operation programming (block 600). Again, the patient 105 can describe the pain he is experiencing (block 605). The clinician then selects a lead 110 for programming (block 610) and performs manual or assisted programming for the lead 110 (block 615). The patient is then scheduled for permanent surgery (block 620).

With permanent surgery (FIG. 15, block 630), the operation is similar to the trial surgery except the IPG 115 is typically inserted into the patient. At block 635, the patient again describes his pain area (block 635), which typically corresponds to the previously described pain area, and the location for lead implant sites can be confirmed. During the procedure, one or more leads 110 are placed in the patient and recorded in the CP (block 640). Also, the IPG 115 is placed in the patient and recorded in the CP 130 (block 640). The camera 380 can be used to capture images of the procedure, capture/read barcode serial numbers of the leads 110, and capture/read barcode serial numbers of the IPG (block 645). Further, fluoroscopy/X-ray images can be recorded in the CP 130, similar to the trial surgery, to help record the procedure (block 645). Next (block 650), the clinician selects the lead 110 for programming. The programming can be manual or assisted (block 655), as already discussed. The process can then be repeated for a next lead 110.

Accordingly, FIGS. 11-15 provide a process for treating a patient using the SCS 100. FIGS. 16-19 provide more detailed processes for performing computer assisted stimulation programming (CASP) using the CP 130. The steps discussed in connection with FIGS. 16-19 will be discussed in an iterative manner for descriptive purposes. Various steps described herein with respect to the process of FIGS. 16-19 are capable of being executed in an order that differs from the illustrated serial and iterative manner of discussion. It is also envisioned that not all steps are required as described below.

Figure 16:
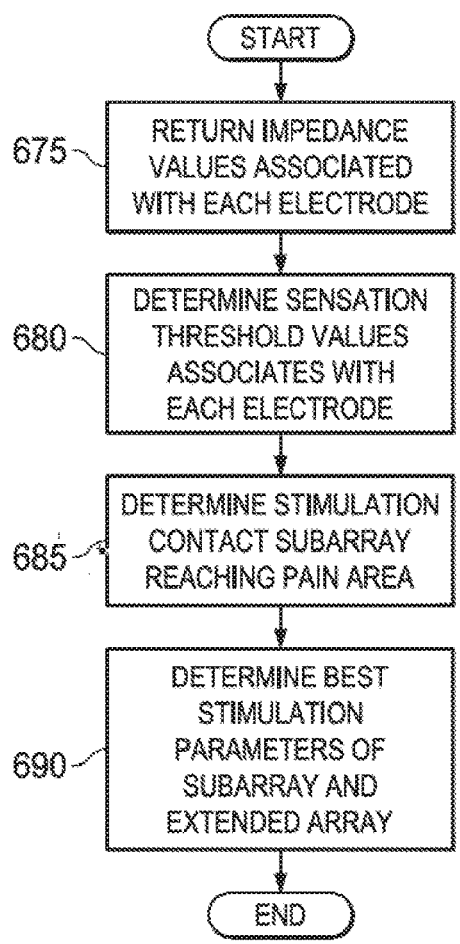
FIG. 16 is a flow diagram of an exemplary computer assisted stimulation programming process for use with the spinal cord stimulation system of FIG. 1.
Figure 17:
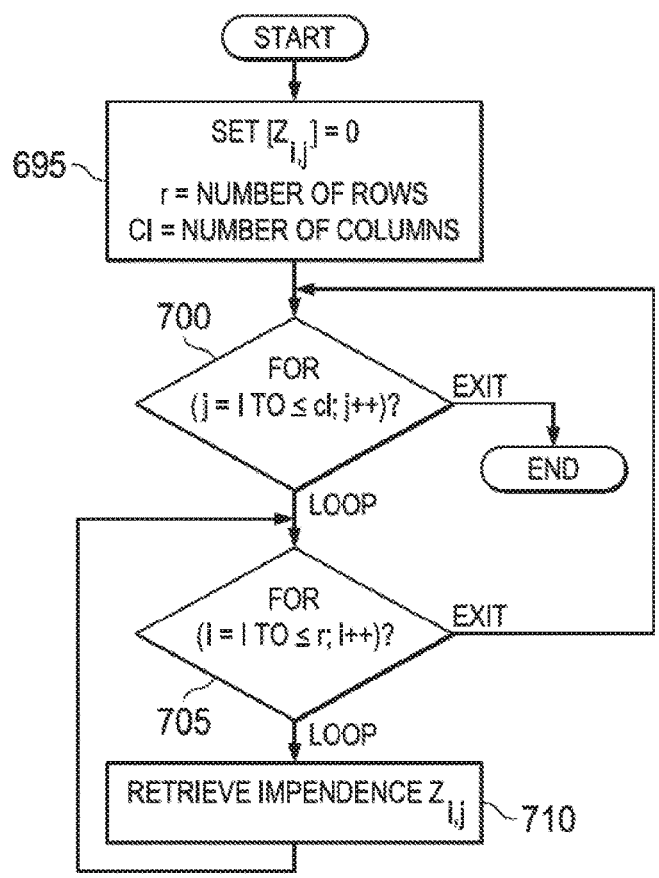
FIG. 17 is a flow diagram of an exemplary process for determining impedance values associated with each electrode.
Figure 18A:
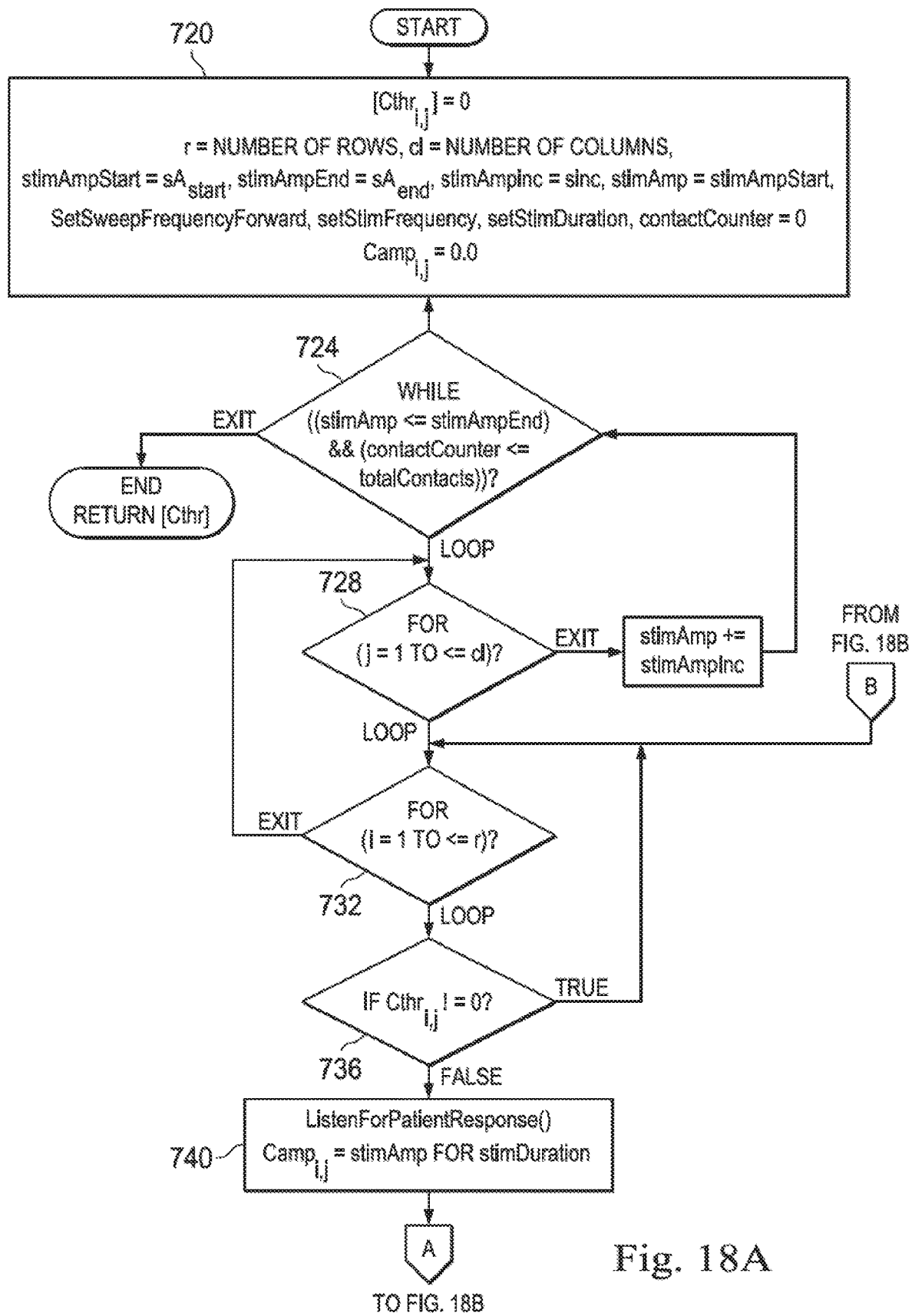
FIGS. 18A and 18B are a flow diagram of an exemplary process for determining perception threshold values associated with each electrode.
Figure 18B:
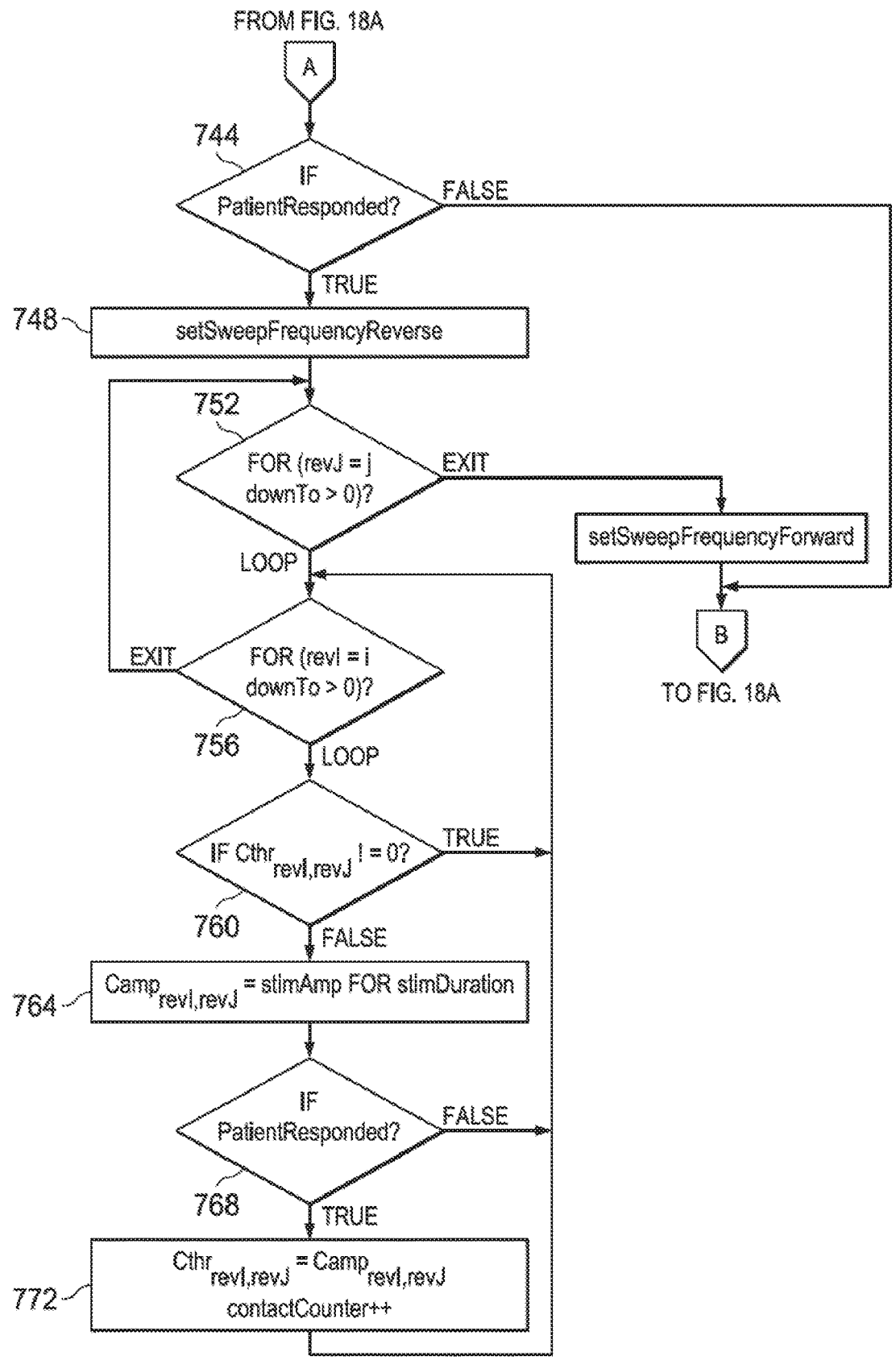
Figure 19:
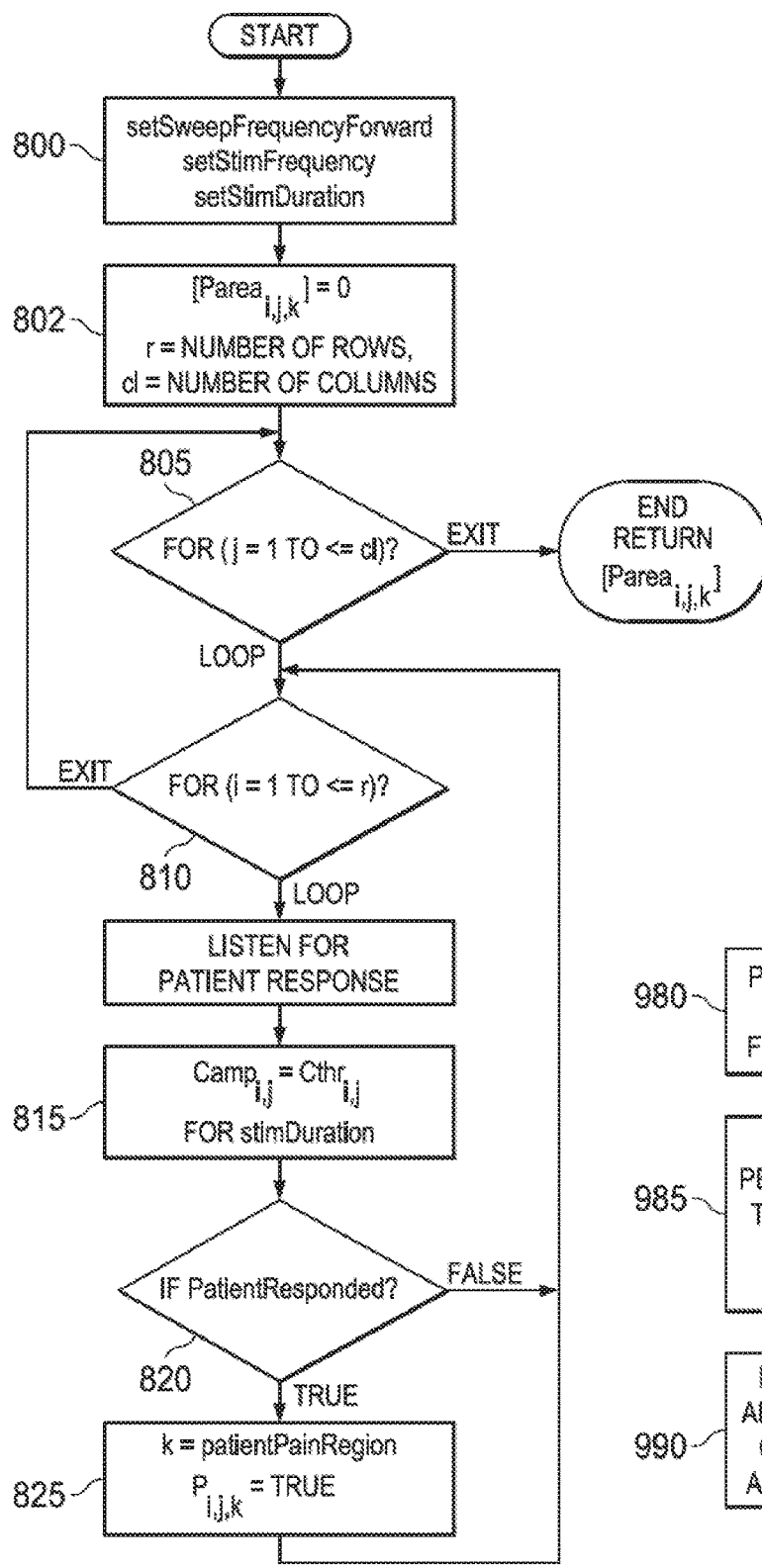
FIG. 19 is a flow diagram of an exemplary process for determining a stimulation electrode sub-array reaching a pain area of the patient.

FIG. 16 shows four exemplary sub-processes of the CASP process. The first process (block 675) retrieves impedance values of the electrodes 150 in a lead 110. In order to perform the process 675, the clinician identifies the lead 110 to the CP 130. The CP 130 knows the arrangement of the electrode array 120, as previously discussed, for the lead 110 once the lead 110 is identified. One exemplary pseudo code and related flow chart for process 675 is shown below and in FIG. 17, respectively. This pseudo code assumes impedance between the contact $Z_{i,j}$, connected lead, the can of the IPG 115, and tissue. However, other impedance combinations are possible between contacts $Z_{i,j}$ and $Z_{k,l}$, where $(k=1:r)$; $(l=1:cl)$ and $(kl=i) \vee (ll=j)$;

Require: EPG or IPG communication established

| | | |
|---|---|---|
| 1: | $[Z_{i,j}] \leftarrow 0$ | >setting impedance array to zero |
| 2: | r ← number of rows | >number of contacts in lead latitudinally |
| 3: | cl ←number of columns | >number of contacts in lead longitudinally |

```
4:  for j = 1 to ≤ cl do
5:      for i = 1 to ≤ r do
6:          Z_{i,j} ← retrieve impedance of contact i, j    >computed by
                                                            IPG/EPG
7:      end for
8:  end for
9:  return [Z_{i,j}]
```

First, the array $[Z_{i,j}]$ is set to zero, the number of rows r is identified, and the number of columns cl is identified (block 695). The array $[Z_{i,j}]$ corresponds to an array representing the electrode array 120. The letter i represents the i-th row from 1 to r rows. The letter j represents the j-th column from 1 to j columns. As discussed previously, the representative array $[Z_{i,j}]$ can represent many electrode arrays, including complex electrode array configurations having "dummy" addresses with "null" values. Therefore, not every address of the array $[Z_{i,j}]$ may include a value. Returning to FIG. 17, the process performs a first for-loop (block 700) for the columns and a second for-loop (block 705) for the rows of the array $[Z_{i,j}]$. The two loops allow the process to progress through each electrode 150 of the electrode array 120 to obtain an impedance value associated with each channel (block 710). Each impedance value relates to the impedance between the can 220 of the IPG 115, the connected lead, tissue, for example, and a respective electrode 150. The process of FIG. 17 helps to determine that the impedance values of lead 110 fall within acceptable ranges, necessary to provide electrical stimulation to the nerves.

Referring back to FIG. 16, the second process (block 680) determines the perception-threshold values of the electrodes 150 in a lead 110. During the process, the patient 105 provides feedback using the PFD 145 when the patient 105 senses a stimulation, such as a paresthesia sensation. One exemplary pseudo code and related flow chart for process 680 is shown below and in FIG. 18, respectively.

```
Require: EPG or IPG communication established
Ensure: Impedance of each contact retrieved
1:   [Cthr_{i,j}] ← 0                                >setting contact stim threshold
                                                      array to zero
2:   r ← number of rows                              >number of contacts in lead
                                                      latitudinally
3:   cl ← number of columns                          >number of contacts in lead
                                                      longitudinally
4:   stimAmpStart ← sA_{start}                       >initial stim amplitude
5:   stimAmpEnd ← sA_{end}                           >ending stim amplitude
6:   stimAmpInc ← sInc                               >stim amplitude increment
7:   stimAmp ← stimAmpStart                          >beginning stimulation
                                                      amplitude
8:   setSweepFrequencyForward                        >activation frequency
9:   setStimFrequency                                >stimulation in pulses per
                                                      seconds
10   setStimDuration                                 >duration of stimulation per
                                                      contact
11:  contactCounter ← 0
12:  Camp_{ij} ← 0
13:  while stimAmp ≤ stimAmpEnd && contactCounter ≤
     totalContacts do
14:      for j = 1 to cl do
15:          for i = 1 to r do
16:              if Cthr_{i,j} ≠ 0 then              >ignore contacts that already
                                                      have
                                                      thresholds established
17:                  continue
18:              end if
19:              listenForPatientResponse( )
20:              Camp_{i,j} ← stimAmp for stimDuration >start
     stimulation
21:              if patientResponded then
22:                  setSweepFrequencyReverse,
     startSweepReverse
23:                  for revJ = j downto revJ > 0 do
24:                      for revI = i downto revI > 0 do
25:                          if Cthr_{revI,revJ} ≠ 0 then>ignore contacts that
     already
                                         have thresholds established
26:                              continue
27:                          end if
28:                          Camp_{revI,revJ} ← stimAmp for stimDuration
     > start
                                         stimulation
29:                          if patientResponded then
30:                              Cthr_{revI,revJ} ← Camp_{revI,revJ}
31:                              contactCounter ++
32:                          endif
```

```
33:            end for
34:         end for
35:       end if
36:       setSweepFrequencyForward
37:     end for
38:   end for
39:   stimAmp+ ← stimAmpInc
40: end While
41: return [Cthr_{i,j}]
```

First the array [$Cthr_{i,j}$] is set to zero, the number of rows r is identified and the number of columns cl is identified (block 720). Also, the initial stimulation amplitude stimAmpStart, the ending stimulation amplitude stimAmpEnd, and the stimulation amplitude increment stimAmpInc are identified; the variable stimAmp is set; and the counter contactCounter is set. Also, the forward sweep frequency setSweepFrequencyForward, the stimulation frequency setStimFrequency, the duration of stimulation setStimDuration are established and the stimulation $Camp_{i,j}$ is tuned off (block 720).

The CASP process performs a while-loop to determine the perception-threshold values of the electrodes 150. The while-loop is performed while the stimAmp value is less than the threshold stimAmpEnd and each contact does not have a perception-threshold value (block 724). The while-loop includes two for-loops: a first for-loop for the columns of the array (block 728) and a second for-loop for the rows of the array (block 732). The two loops allow the CASP process to progress through each electrode 150 of the electrode array 120. While performing the loops, the process determines whether the perception array does not have a perception value for the i-th row and the j-th column (block 736). If the array location has a perception-threshold value, then the process returns to block 732. Otherwise, the process continues.

Before proceeding further, it should be noted that the CASP process automatically and systematically progress through the electrodes 150. In addition, as shown by block 736, the CASP process "skips" or passes over an electrode $C_{i,j}$ once a perception threshold $Cthr_{i,j}$ is identified for the electrode 150. However, the sweeping of the electrodes 150 is still automated and systematic even when this skip process occurs.

Referring now to block 740, the contact amplitude $Camp_{i,j}$ is set to the stimulation amplitude stimAmp, the process pauses for a duration. At the same time the CASP is monitoring for a patient response. For the implementation discussed herein, the stimulation amplitude is a current amplitude. However, a voltage amplitude or other variable (pulse shape, frequency, width, etc.) can be used and adjusted in place of the current amplitude. If the patient 105 feels a sensation, then they provide feedback to the CP 130 via the PFD 145 (block 744). If a patient 105 response is detected then the process proceeds to block 748. Otherwise, the CASP process continues to proceed through the for-loops.

When a patient 105 provides feedback indicating a response, a reverse frequency is set (block 748) and the sweep is reversed (starting at block 752). More specifically, for the CASP process discussed herein, the process proceeds quickly through the electrode array 120 and a delayed reaction from the patient 105 is expected. By performing a reverse sweep, the CASP process more accurately confirms a response. The CASP process initiates two for-loops 752-756 in a reverse sweep direction. While performing the reverse sweep, the process "skips" or passes over electrodes 150 having perception thresholds (block 760). The contact amplitude $Camp_{revI,revJ}$ is set to the stimulation amplitude stimAmp, the process pauses for a duration (block 764). If a patient 105 feels a sensation, then they provide feedback to the CP 130 with the PFD 145. If a patient 105 response is detected (768), then the process proceeds to block 772. Otherwise, the CASP process continues to proceed through the for-loops 752 and 756. At block 772, the perception-threshold value is set for $Cth_{revI,revJ}$ and the contactCounter increments.

Upon completion of the perception threshold sweep, perception thresholds [$Cthr_{i,j}$] are established for each contact 150. The values of the perception-threshold sweep are used to normalize the initial sensation felt by the patient with each channel/electrode 150.

Referring again to FIG. 16, the third process (block 685) performs a pain-area sweep to determine the best electrode(s) 150 for stimulating neurons to the affected pain area. During this process, the patient 105 again provides feedback using the PFD 145 when the patient 105 senses a defined stimulation. One exemplary pseudo code and related flow chart for process 685 is shown below and in FIG. 19, respectively.

```
Require: [Cthr_{i,j}] ≠ 0                          >threshold array is not empty
Ensure: stimulation contacts that cover pain
1:    [Parea_{i,j,k}] ← false
2:    setSweepFrequencyForward                    >activation frequency
3:    setStimFrequency                            >stimulation in pulses per
                                                   seconds
4:    setStimDuration                             >duration of stimulation per
                                                   contact
5:    r ← number of rows                          >number of contacts in lead
                                                   latitudinally
6:    cl ← number of columns                      >longitudinal columns
7:    for: j = 1 to ≤ r do
8:       for i = 1 to ≤ cl do
9:          listenForPatientResponse( )
10:         Camp_{i,j} ← Cthr_{i,j} for stimDuration >start stimulation
```

```
11:       if patientResponse then
12:           k ← patientPainRegion > patient locates
where pain
              region is
13:           PainA_{i,j,k} ← true
14:       end if
15:   end for
16:   end for
17:   return [Parea_{i,j,k}]
```

First, the forward sweep frequency setSweepFrequencyForward, the stimulation frequency setStimFrequency, the duration of stimulation setStimDuration are established and the stimulation Camp$_{ij}$ is tuned off (block 800). Next, the number of rows r is identified, the number of columns cl is identified, and the array [Parea$_{i,j,k}$] is set to false (block 802). The CASP process then automatically and systematically progresses through the electrodes 150. A first for-loop (block 805) for the columns of the area and a second for-loop (block 810) for the rows of the array are swept. While performing the loops, the electrode Camp, is set to the threshold Cthr$_{i,j}$, which may be set from the prior perception-threshold sweep (block 815). The process pauses for a duration. If the electrode 150 stimulates neurons related to the pain area, then the patient 105 provides feedback to the CP 130 via the PFD 145. If a patient 105 response is detected (block 820) then the process proceeds to block 825. Otherwise, the CASP process continues the automated and systematic sweep through the electrodes 150. At block 825, the patient identifies the paresthesia area (k) the stimulation is reaching and contact i,j in the array [Parea,$_{i,j,k}$] is set to true.

In some implementations, when a patient 105 provides feedback indicating a response to the stimulation that reaches the pain area, the sweep can be repeated multiple times over. The resulting multitude pain area arrays can be compared to verify consistent patient response. However, the exemplary process shown in FIG. 19 does not include the repeated sweep.

At the end of the pain-area sweep, the CP 130 identifies the best electrode(s) 150 for stimulating neurons to the affected pain area, i.e., to provide paresthesia to the affected pain areas. It is envisioned that the process of performing the perception threshold sweeps and pain area sweeps can be performed in less than thirty minutes, and preferably in less than ten minutes. The time can vary based on the sweep speed and delay times used during the sweep. The CP 130 can then isolate the resulting best electrodes and refine the stimulation parameters (amplitude, frequency, pulse width) to result in an optimal pattern as has been previously done in prior SCS systems (block 690 of FIG. 16).

Thus, the invention provides, among other things, useful and systems and methods for providing electrical stimulation to a neural tissue of a patient.

The discussions above pertain to systems and methods of providing CASP according to some embodiments of the present disclosure. Discussed below are systems and methods of providing CASP according to some alternative embodiments of the present disclosure. Hereinafter, the CASP process discussed above is referred to as conventional CASP, and the CASP process discussed below is referred to as alternative CASP. For reasons of consistency and clarity, similar elements and components appearing in figures pertaining to conventional CASP and alternative CASP are labeled the same.

Figure 20:
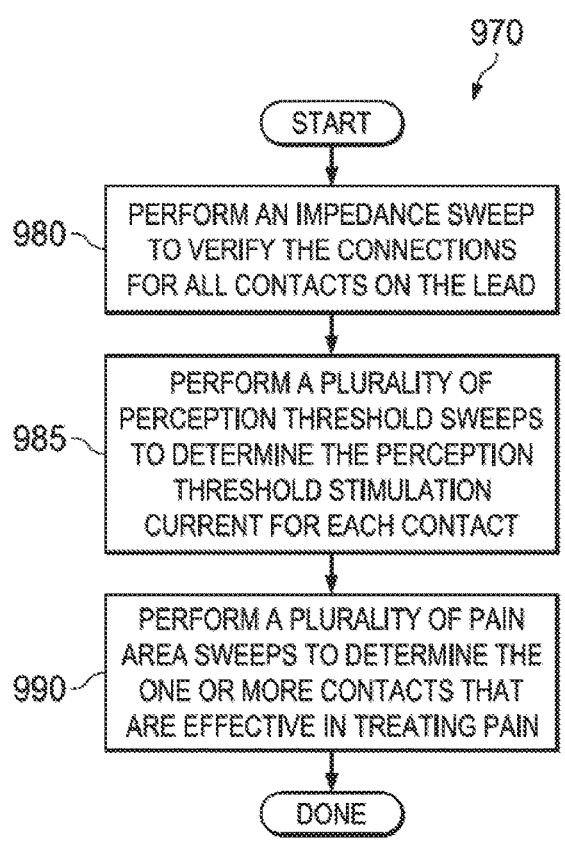
FIGS. 20, 31 and 35 are flowcharts illustrating various methods for performing computer assisted stimulation programming according to various embodiments of the present disclosure.

Referring now to FIG. 20, a flowchart of a simplified method 970 of performing alternative CASP. Similar to the embodiments of the CASP process discussed above, the alternative CASP method includes three different sweeps. The first sweep is an impedance sweep in a step 980, in which an impedance sweep is performed to check the electrical and/or physical connections for all contacts on the lead. In various embodiments, the impedance sweep in step 980 is similar to the impedance sweep in block 575 of the conventional CASP discussed above with reference to FIG. 13. By applying an electrical current and measuring the corresponding voltage (or vice versa) for each contact, the respective impedance for each contact is calculated. If the impedance falls within an acceptable range, the connection associated with that contact is deemed to be good. Otherwise, if the impedance is too high or too low, it may indicate an open circuit or short circuit condition, and further investigation or troubleshooting may be needed, since open or short circuit conditions are not desirable for a lead and should be corrected. The impedance values may also be visually displayed on a screen of the clinician programmer.

Still referring to FIG. 20, the method 970 of performing alternative CASP includes a step 985, in which a plurality of perception threshold sweeps is performed to determine the perception threshold stimulation current for a plurality of contacts on the lead. For example, the plurality of contacts for which the perception threshold sweeps should be performed are the contacts that have been deemed to be "good" contacts based on the impedance sweep of step 980. In other words, the "bad" contacts that have connection problems (determined based on impedances that are too high or too low from the impedance sweep) are excluded from the perception threshold sweep.

The method 985 is the second sweep of the alternative CASP process. The step 985 shares some similarities with the perception threshold sweep in block 580 of the conventional CASP discussed above with reference to FIG. 13, but is different in certain other aspects. For example, the goal for both the conventional CASP and the alternative CASP is to determine, for each contact, the amount of stimulation current that causes the patient to feel a stimulation sensation.

However, conventional CASP and alternative CASP implement different algorithms to determine the perception threshold for each contact. As discussed above, conventional CASP performs a "linear" sweep for all contacts. That is, the stimulation current is ramped up from a low value (e.g., zero) to a high number for each contact. During this process, the patient will provide feedback—for example by engaging the PFD 145 discussed above with reference to FIG. 1—to let the healthcare professional know when the perception threshold is reached. In other words, the patient will inform the healthcare profession when he/she finally begins to "feels some amount of stimulation" when a certain stimulation current amplitude is reached. This procedure is performed for each contact one by one, until the perception threshold is determined for all the contacts.

Unlike the conventional CASP, the alternative CASP employs a sub-dividing approach to quickly separate the contacts into smaller and smaller groups in order to identify the one or more contact of interest. To explain this approach in more detail, referring now to FIGS. 21-25, which are simplified diagrammatic illustrations of an example lead 1000 according to some embodiments. The lead 1000 has contacts 1010A-1010L (also referred to as electrodes). For all the contacts 1010, stimulation current is simultaneously ramped up from zero slowly, for example by small increments (e.g., 0.05 mA or 0.1 mA) with pauses in between each increment (e.g., a few seconds or longer). In some embodiments, the exact configurations for the ramping up process may be set by a healthcare professional.

As this ramping up process takes place, the patient is asked to provide feedback, for example by engaging the PFD 145 discussed above. In some embodiments, the patient's engagement of the PFD 145 will generate a signal (e.g., generated by the PFD 145) that will be sent to the clinician programmer. This signal informs the clinician programmer that a perception threshold has been reached for at least one of the contacts on the lead, and therefore the current ramping process should be temporarily paused until such contact can be identified. Alternatively, a human assistant may also be employed instead of, or in addition to, the PFD 145 to help the patient provide feedback.

Figure 21:
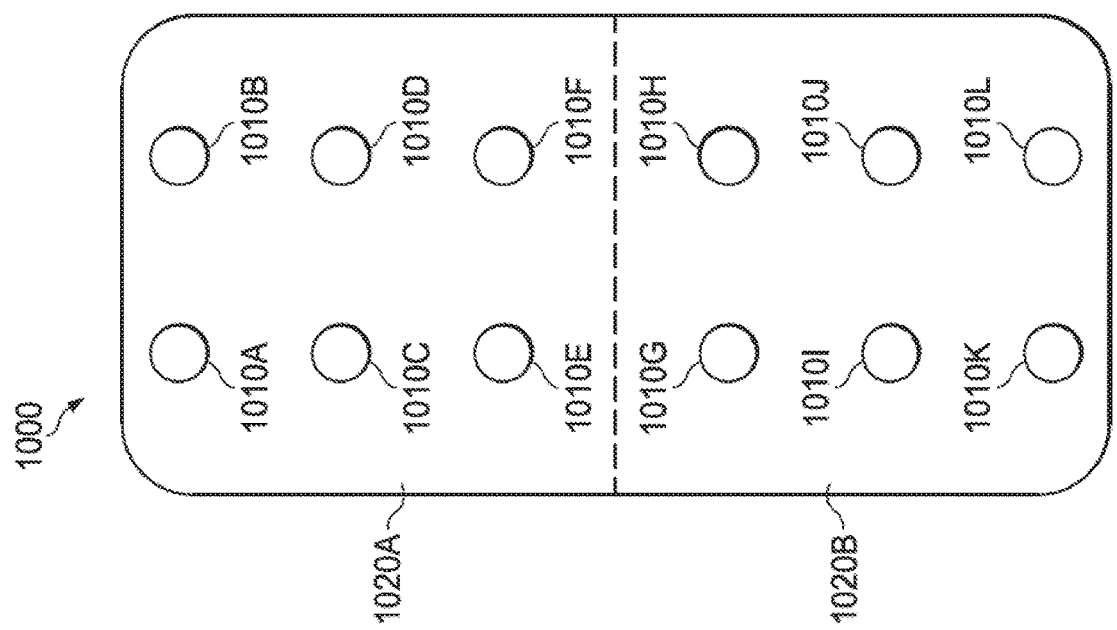

In any case, when the patient indicates that he/she is beginning to feel some stimulation sensation, the value of the stimulation current amplitude that produced the stimulation sensation is recorded. This value may be stored in the local memory storage of the clinician programmer, in the IPG, or in a server (i.e., cloud) located remotely from the clinician programmer. In addition, the contacts 1010A-1010L on the lead 1000 are divided into a plurality of sections or groups, for example into two sections 1020A (containing contacts 1010A-1010F) and 1020B (containing contacts 1010G-1010L), as shown in FIG. 21. The contacts 1010A-1010I are then activated one section or group at a time by applying the recorded stimulation current to all the contacts in that activated section, and the patient is asked if the stimulation sensation is still being felt.

For example, suppose that the stimulation current that produced the stimulation sensation for the patient is 1.5 mA. The contacts 1010A-1010F in the section 1020A are then turned on at 1.5 mA, while the contacts 1010G-1010L are turned off. The patient provides feedback by engaging or not engaging the PFD 145 to indicate whether or not the stimulation sensation is still being felt. If the PFD 145 is engaged, that indicates the patient feels the stimulation sensation while the section 1020A is activated, which means the contact (or contacts) producing the stimulation sensation resides in section 1020A. If the PFD 145 is not engaged, that indicates the patient does not feel any stimulation sensation while the section 1020A is activated, which means the contact (or contacts) producing the stimulation sensation resides in section 1020B. In any case, based on the patient's feedback, the section in which the stimulation-sensation-producing contact (or contacts) resides is investigated further.

Figure 22:
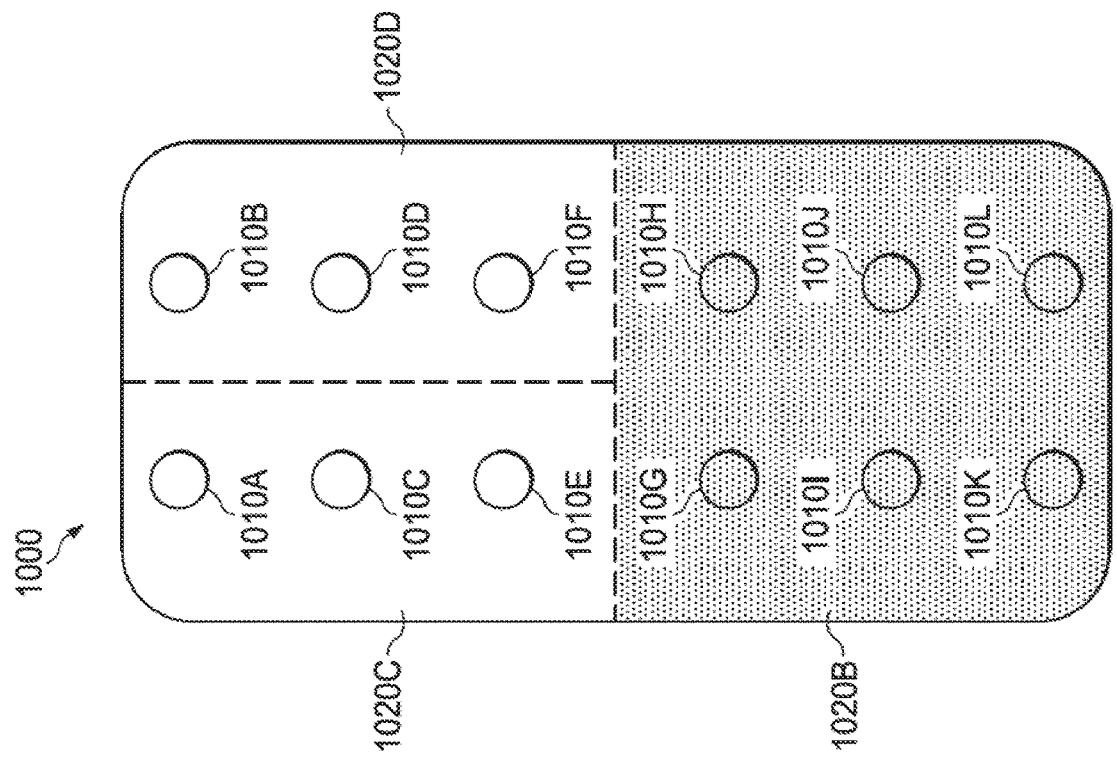
FIGS. 21-25 are simplified diagrammatic illustrations of an example lead that contains a plurality of contacts according to various embodiments of the present disclosure.

For the purposes of providing an example, referring to FIG. 22, suppose the patient feels a stimulation sensation when the section 1020A is activated. Thus, the section 1020B is temporarily crossed-off (i.e., not being considered for further investigation at this time). This is visually represented herein by the shading of the section 1020B in FIG. 22. The section 1020A is of interest (i.e., likely containing the contact that caused the stimulation sensation), and it is further sub-divided into sections 1020C (containing contacts 1010A/C/E) and 1020D (containing contacts 1010B/D/F). The contacts 1010A/C/E in the section 1020C are then turned on at 1.5 mA, while the contacts 1010B/D/F are turned off. Again, the patient provides feedback by engaging or not engaging the PFD 145 to indicate whether or not the stimulation sensation is still being felt. If the PFD 145 is engaged, that indicates the patient feels the stimulation sensation while the section 1020C is activated, which means the contact that caused the stimulation sensation resides in section 1020C. Otherwise, the contact that caused the stimulation sensation resides in section 1020D.

Figure 23:
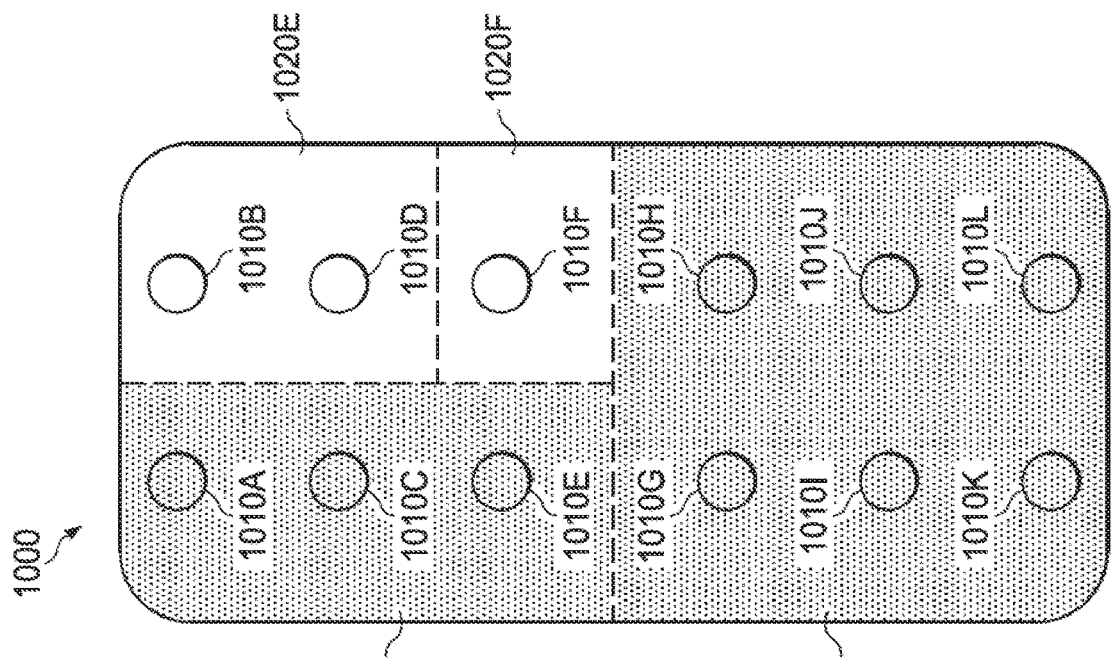

Suppose the patient does not engage the PFD 145 while the section 1020C is activated but does engage the PFD 145 while the section 1020D is activated. Therefore, the section 1020D is investigated further, and the section 1020C is crossed off, as shown in FIG. 23. At this point, the three contacts 1010B/D/F does not necessarily need be divided anymore, since three contacts cannot be evenly divided by two. In other words, the sub-division algorithm discussed herein may round down if a sub-division results in a fraction or a decimal: in this case, 3 divided by 2=1.5, which is rounded down to 1. In other words, each contact 1010B/D/F may be individually tested to determine whether the contact is the contact that produced the stimulation sensation, and if so, that contact is assigned 1.5 mA as the perception threshold. For example, the patient may confirm that both the contacts 1010B and 1010D produced the stimulation sensation, but the contact 1010F did not. Thus, the perception threshold for contacts 1010B and 1010D are assigned to be 1.5 mA in this example.

Figure 24:
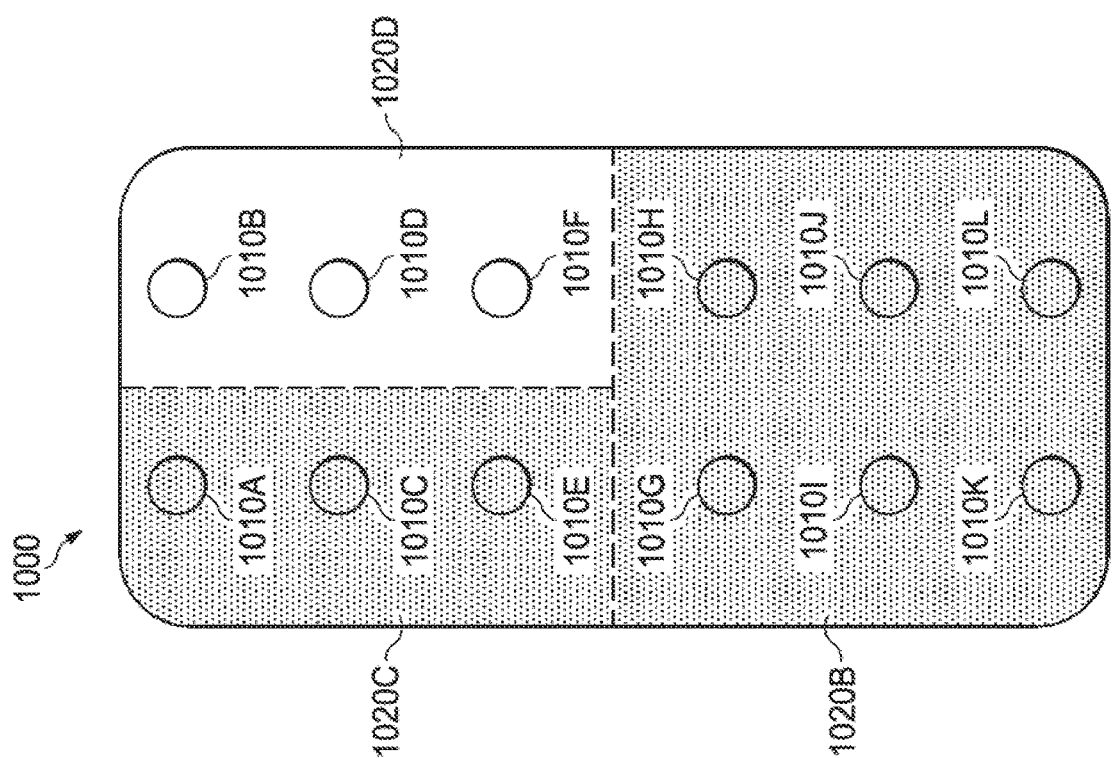
Figure 25:
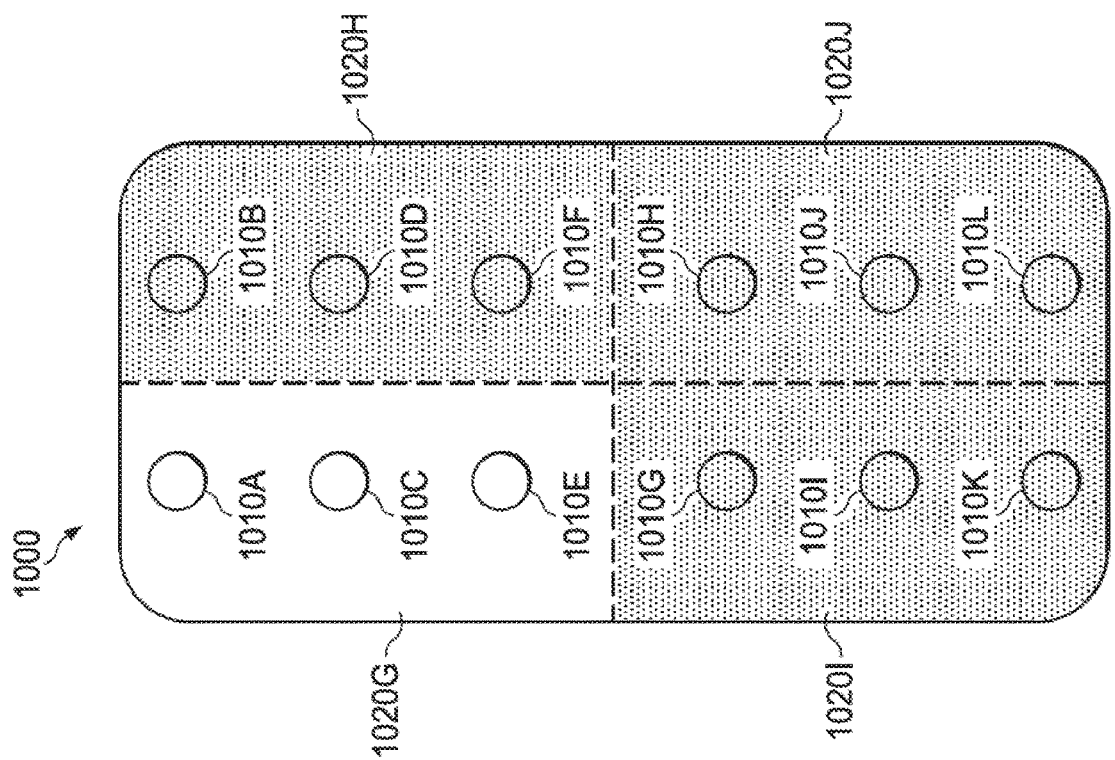

Alternatively, as shown in FIG. 24, the contacts 1010B/D/F in the section 1020D may still be sub-divided again into a section 1020E containing any of the two contacts (e.g., contacts 1010B/D) and another section 1020F containing the remaining contact (e.g. contact 1010F). The procedure discussed above is repeated for these sections 1020E and 1020F, until the patient can confirm which one or more of the contacts actually produced the stimulation sensation. Based on the same example discussed above, the patient should confirm that the contacts 1010B and 1010D are the contacts that caused the stimulation sensation, and 1.5 mA is assigned as the perception threshold for these contacts.

In any case, after the perception threshold for contacts 1010B and 1010D are determined, contacts 1010B and 1010D are "eliminated" or "excluded" from the subsequent alternative CASP analysis. In other words, the contacts 1010B and 1010D are no longer turned on, since their corresponding perception threshold is already known (i.e., 1.5 mA in this example). For the remaining contacts 1010A, 1010C, and 1010E-1010L, the ramping up of the stimulation current is resumed up from a current amplitude greater than the perception threshold identified for the contacts 1010B and 1010D. In this example, since the perception threshold for the contacts 1010B and 1010D is determined to be 1.5 mA, the ramping up for the remaining contacts may start from a current slightly greater than 1.5 mA, for example 1.6 mA.

The ramping up process may continue by incrementing the stimulation current 0.1 mA at a time (or by another suitable small increment step), until the patient feels a stimulation sensation again. At that point, the remaining contacts are sub-divided into a plurality of sections and tested again in a similar process as discussed above, in order to narrow down the contact that caused the stimulation sensation. For example, after a plurality cycles of sub-dividing and testing processes, the contacts 1010A and 1010C are determined to have a perception threshold at 1.8 mA. Thereafter, the contacts 1010A and 1010C are eliminated from the remaining alternative CASP analysis, along with the contacts 1010B and 1010D that have been previously eliminated.

For the remaining contacts 1010E-1010L, the process discussed above is repeated again and again a plurality of times, until the perception threshold for every contact has been determined. For reasons of simplicity, the details of these processes are not discussed herein, though it is understood that the perception threshold determination for each contact may involve one or more stimulation ramping and sub-dividing processes for the contacts. It is also understood that although the description of the alternative CASP process may appear to be lengthy and time-consuming, in reality it can be performed quite quickly. This is at least in part due to the fact that the current ramping and contact sub-dividing processes in the alternative CASP analysis are computer-automated, for example by the electronic processors and memory in the clinician programmer. In some embodiments, the entire alternative CASP process may be completed in a few minutes. This is beneficial, because the CASP process is often performed during exploratory surgery or permanent implant surgery, while the patient is under anesthesia. Therefore, the fast performance of the alternative CASP process may lead to better patient satisfaction and/or greater accuracy for the determination of the perception thresholds for the contacts.

It is understood that the sub-dividing process discussed above with reference to FIGS. 21-25 is merely a simplified example of how a plurality of contacts on a lead may be divided and sub-divided into smaller and smaller groups in order to zero in on the contact(s) of interest. For example, the dividing and sub-dividing process in this example utilizes a binary division algorithm, which attempts to divide the contacts into two groups of approximately equal number of contacts by each division. In other words, the contacts are divided by two in most situations (until it is not feasible to do so anymore).

In other embodiments, the contacts may be divided and sub-divided by different algorithms. For example, referring to FIG. 25, as the patient first feels stimulation as the current is being ramped up, the contacts 1010A-1010L may be divided into four quadrant sections 1020G, 1020H, 1020I, and 1020J each containing their respective contacts. The quadrant sections 1020G/H/I/J may then be activated one section at a time to locate the quadrant section in which the contact that caused the stimulation sensation resides. This process may be repeated a number of times until the contact that caused the stimulation sensation is located, and the amount of stimulation current that caused the stimulation sensation is then assigned as the perception threshold to that contact. Similarly, the contacts may be divided and sub-divided into any other number of sub-groups in other embodiments. For example, in some embodiments, as the stimulation current is being ramped up initially, once the patient indicates that he/she feels a stimulation sensation, the ramping is paused, and then each contact is interrogated individually to determine if that contact was the one that caused the patient to feel the stimulation sensation. Alternatively stated, it is as if the contacts are divided into a plurality of "groups" that each contain just one respective contact, rather than groups that contain more than one contact. Furthermore, in certain embodiments, each sub-division may be performed differently than previous sub-divisions. For example, a group of contacts may first be divided into two groups, and then each group may be subsequently divided into three sub-groups, and each sub-group may then be subsequently divided into four sub-sub-groups, etc.

It is also understood that there may be an upper limit or maximum level as to how much the stimulation current can be ramped up. For example, for the patient's safety, the upper limit for the stimulation current may be set at 15 mA (or another suitable number). If the ramping up process has been performed such that the stimulation current is now at 15 mA, and one or more contacts still have not caused the patient to feel any stimulation sensation, then the ramping up process will stop anyway, and the upper limit for the stimulation current (15 mA in this example) will be assigned as the perception threshold for these contacts. The rationale is that it can be safely assumed that the patient can be stimulated with these contacts driven by stimulation currents at the upper limit, and the patient will not experience any discomfort as a result of it. For the rest of the contacts that have perception thresholds lower than the upper limit, however, they should be driven by stimulation currents equal to their respective perception thresholds when activated.

Referring back to FIG. 20, the method 900 of performing alternative CASP includes a step 990, in which one or more pain area sweeps are performed to locate the contacts that offer the best stimulation for the patient's pain areas. This is also known as a Paresthesia sweep, since Paresthesia refers to the feeling of stimulation in the areas of pain. The step 990 is the third sweep of the alternative CASP process. In some embodiments, the pain area sweep of step 990 may be substantially similar or identical to the pain area sweep in block 585 of the conventional CASP process shown in FIG. 13. In other embodiments, the step 990 shares some similarities with the block 585 of the conventional CASP process, but is different in certain other aspects. For example, the step 990 may perform the pain area sweep using a division algorithm similar to the algorithm used to perform the perception threshold sweep.

For example, in an embodiment using a binary division, the contacts are divided into two (or another suitable number) different sections or groups. For each section, stimulation currents are applied to each of the contacts in that section, where the stimulation current amplitude is set to the respective perception threshold that had been determined for that contact. The patient is then asked to provide feedback (e.g., via engagement with the PFD 145) as to whether or not he/she feels relief at the target area of pain (e.g., knee, shoulder, etc.). Based on the patient's feedback, the contacts in the section/group of interest are sub-divided one or more times into smaller and smaller sections/groups, until the target contacts that offered pain relief are identified. In other words, the patient feels Paresthesia when these target contacts are driven by the stimulation current at their respective perception thresholds.

Again, the division or sub-division of the contacts in the pain area sweep process need not be binary, as the contacts may be divided into any other number of groups containing any suitable number of contacts in a manner similar to that discussed above with reference to the perception threshold sweep process. In the alternative embodiment discussed above where the contacts are separated individually (i.e., into "groups" that each contain just a single respective contact), the pain area sweep process may be performed by activating each of the contacts by applying their respective perception threshold stimulation current, and determining whether the patient experiences Paresthesia when such contact is activated. In this manner, the pain area sweep involves a single division process (i.e., dividing the group of contacts into individual contacts), and therefore no further sub-division is necessary.

In any case, once the target Paresthesia-producing contacts are identified, they may then be saved (e.g., in a local or remote memory storage) and thereafter used to develop a treatment protocol for providing therapeutic electrical stimulation to treat the patient. In some embodiments, the treatment protocol may be developed manually by the healthcare professional. For example, the healthcare professional may manually configure the stimulation parameters such as stimulation current amplitude, frequency, pulse width, etc., for these target contacts. In some other embodiments, the clinician programmer may be able to automatically develop one or more treatment protocols based on the identified target contacts.

In the perception threshold sweep and/or the pain area sweep discussed above, the dividing and sub-dividing processes may be performed dynamically (i.e., "on the fly") in some embodiments. For example, the dividing and sub-dividing algorithms will continue to divide the remaining contacts by a factor of two (or another number) in each cycle, until a fraction or a decimal is reached (meaning the remaining contacts can no longer be divided in equal numbers). At that point, the number of divided contacts is rounded down. For example, if three contacts are remaining, the contacts will be sub-divided into three individual contacts (3/2=1.5, which is rounded down to 1). As another example, if five contacts are remaining, the contacts may be sub-divided into a group containing two contacts and another group containing three contacts. Of course, alternative algorithms may be used to carry out the sub-division processes.

In some other embodiments, the lead contact configuration information (e.g., information regarding the number of contacts on the lead, and how these contacts are arranged) is retrieved by the clinician programmer, for example via telecommunications conducted between the clinician programmer and the IPG before the alternative CASP process is performed. The clinician programmer may store a look-up table in its local memory (or remotely) that describes how the contact division and sub-division discussed above should be performed for each type of lead. In this manner, the contact division and sub-division need not necessarily be performed dynamically, but it may be performed according to a predefined arrangement based on the lead contact configuration.

As discussed above, a portable electronic device such as a clinician programmer may be used to carry out various aspects of the CASP and alternative CASP processes discussed above. FIGS. 26-30 are example screenshots of a user interface 1200 for visually representing different aspects of the CASP and alternative CASP processes according to the various aspects of the present disclosure. In some embodiments, the user interface 1200 may be displayed on a screen of a clinician programmer. In some embodiments, the screen may be a capacitive or resistive touch-sensitive screen. In other embodiments, the screen may be a non-touch-sensitive screen, for example a Liquid-Crystal Display (LCD) screen, a Light-Emitting Diode (LED) screen, or a Cathode Ray Tube (CRT) screen. In yet other embodiments, the user interface 100 may be displayed on a programmer and an external monitor simultaneously, for example in accordance with U.S. patent application Ser. No. 13/600,875, filed on Aug. 31, 2012, entitled "Clinician Programming System and Method", attorney docket 46901.11/QIG068, the disclosure of which is hereby incorporated by reference in its entirety. As such, both the healthcare provider and the patient are able to view the user interface at the same time.

Figure 26:
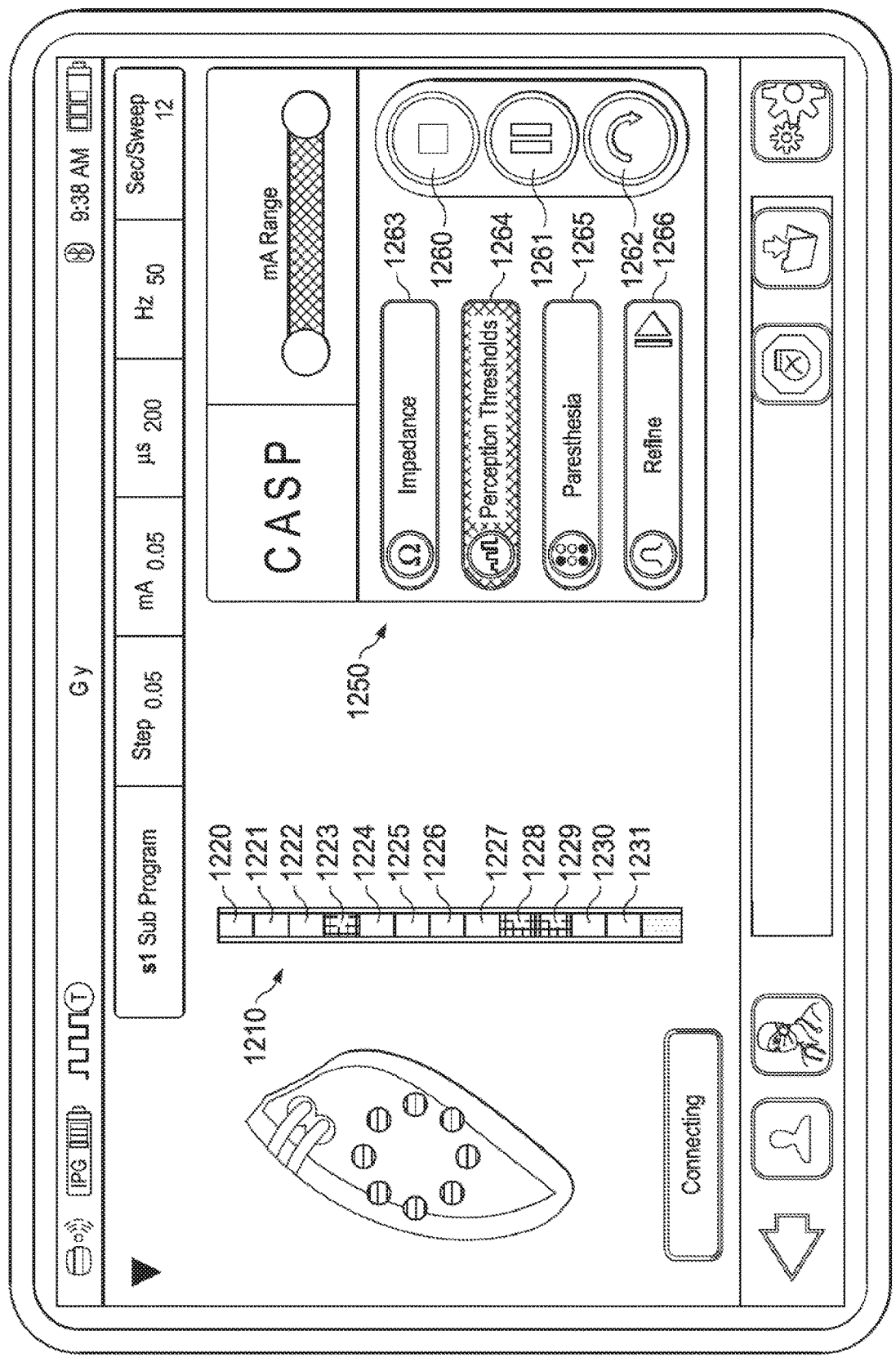

Referring to FIG. 26, the user interface 1200 illustrates an example lead 1210 (or a virtual representation thereof). In this example, the lead 1210 is a single column lead and contains twelve contacts 1220-1231. Of course, this is just an example, and other types of leads may be implemented in alternative embodiments. The user interface 1200 also illustrates a CASP programming window 1250. The CASP programming window includes virtual buttons 1260-1266. Each of the virtual buttons 1260-1266 may be user-engageable, for example by a touch input (e.g., either with a finger or a stylus), or a hover input, or by a mouse and/or keyboard.

In this example, the virtual button 1260 is a "start/stop" button that when engaged, will execute the CASP or alternative CASP processes discussed above. The virtual button 1261 is a "pause" button that when engaged, will pause the CASP or alternative CASP processes discussed above. The virtual button 1262 functions similar to a "debug" command in a computer programming environment. In other words, when the virtual button 1262 is engaged, it temporarily pauses the CASP or alternative CASP processes and allows the user to "single-step" through the execution of the CASP or alternative CASP processes. Thus, the engagement of the virtual button 1262 allows the execution of one of the sweep processes to be paused. The user may then advance the pace of the sweep at his/her own discretion.

The virtual buttons 1263-1265 correspond to the impedance sweep, the perception threshold sweep, and the pain area sweep (i.e., the Paresthesia sweep) sweep discussed above, respectively. When the virtual button 1260 is engaged to begin the sweeping processes, the impedance sweep would first be performed, followed by the perception threshold sweep, and then the pain area sweep. While each type of sweep is occurring, the corresponding virtual button 1263-1265 may be highlighted to indicate the type of sweep that is occurring.

In the example shown in FIG. 26, the impedance sweep has already occurred, and now the perception threshold sweep is underway, as indicated by the highlighting of the virtual button 1264. Also, in this example, the impedance sweep has identified the contacts 1223 and 1228-1229 as "bad" contacts, which indicate connection problems. As such, these contacts 1223 and 1228-1229 are excluded from the perception threshold sweep (and thereafter the pain area sweep). To remind the user of their exclusion, the contacts 1223 and 1228-1229 may be visually distinguished from the rest of the contacts. For example, the contacts 1223 and 1228-1229 may be colored or shaded differently than the rest of the contacts.

As discussed above, the perception threshold sweep begins by ramping up the stimulation current for a plurality of contacts. Had the impedance sweep identified no "bad" contacts, all contacts 1220-1231 would have been included in this ramping up process. However, in this example, the plurality of contacts whose currents are being ramped up includes the contacts 1220-1222, 1224-1227, and 1230-1231, but not the "bad" contacts 1223, 1228, and 1229. In some embodiments, the contacts 1220-1222, 1224-1227, and 1230-1231 that are undergoing the ramping up process are visually distinguished by flashing. In other embodiments, the visual distinction of these contacts may be a particular coloring or shading that is only present while the ramping up process is underway. Note that in the conventional CASP process, each contact may be ramped up individually, and therefore only one contact may be flashing (or otherwise visually distinguished) at a time. For reasons of simplicity, this is not specifically illustrated herein.

Figure 27:
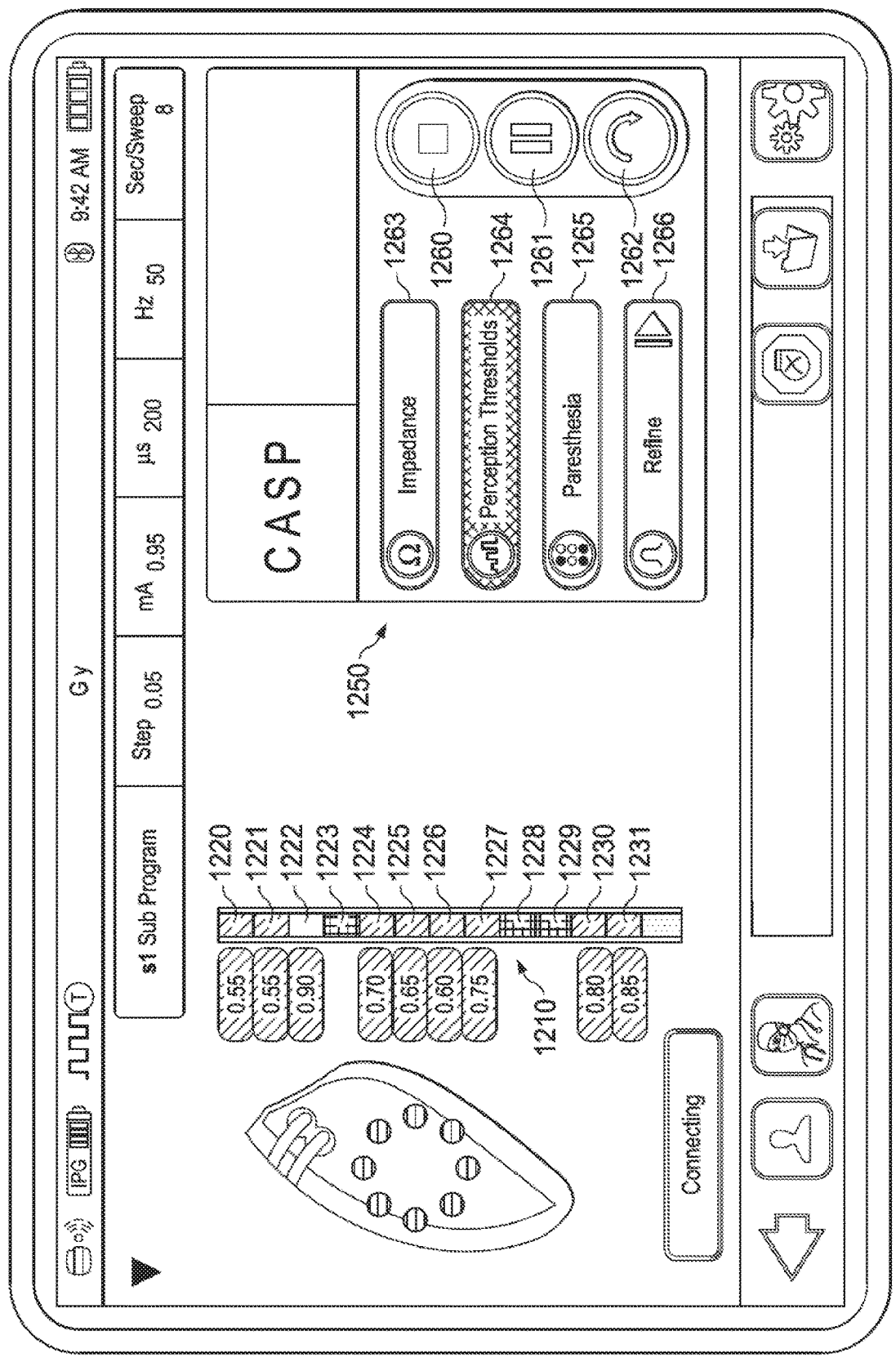

Referring now to FIG. 27, after the perception thresholds have been determined for one or more of the plurality of contacts 1220-1222, 1224-1227, and 1230-1231 (either through the conventional CASP process or the alternative CASP process), these contacts may also be given a different visual distinction. In this example, the respective perception thresholds for contacts 1220-1221, 1224-1227, and 1230-1231 have been determined, and therefore these contacts may stop flashing and may be given a color (e.g., green) different from the color (e.g., yellow) of the "bad" contacts 1223 and 1228-1229 that were excluded from the perception threshold sweep.

Furthermore, the numeric values of the perception thresholds may also be visually displayed next to their respective contacts 1220-1221, 1224-1227, and 1230-1231. In this example, the numeric values of the perception thresholds for the contacts 1220-1221, 1224-1227, and 1230-1231 are (in mAs) 0.55, 0.55, 0.90, 0.70, 0.65, 0.60, 0.75, 0.80, and 0.85, respectively. In addition, the perception threshold for the contact 1222 is still to be determined, and thus the stimulation current is still being ramped up for the contact 1222. The value of the stimulation current during the ramping up process may also be displayed adjacent to the corresponding contacts, in this case 0.90 mA for the contact 1222.

Figure 28:
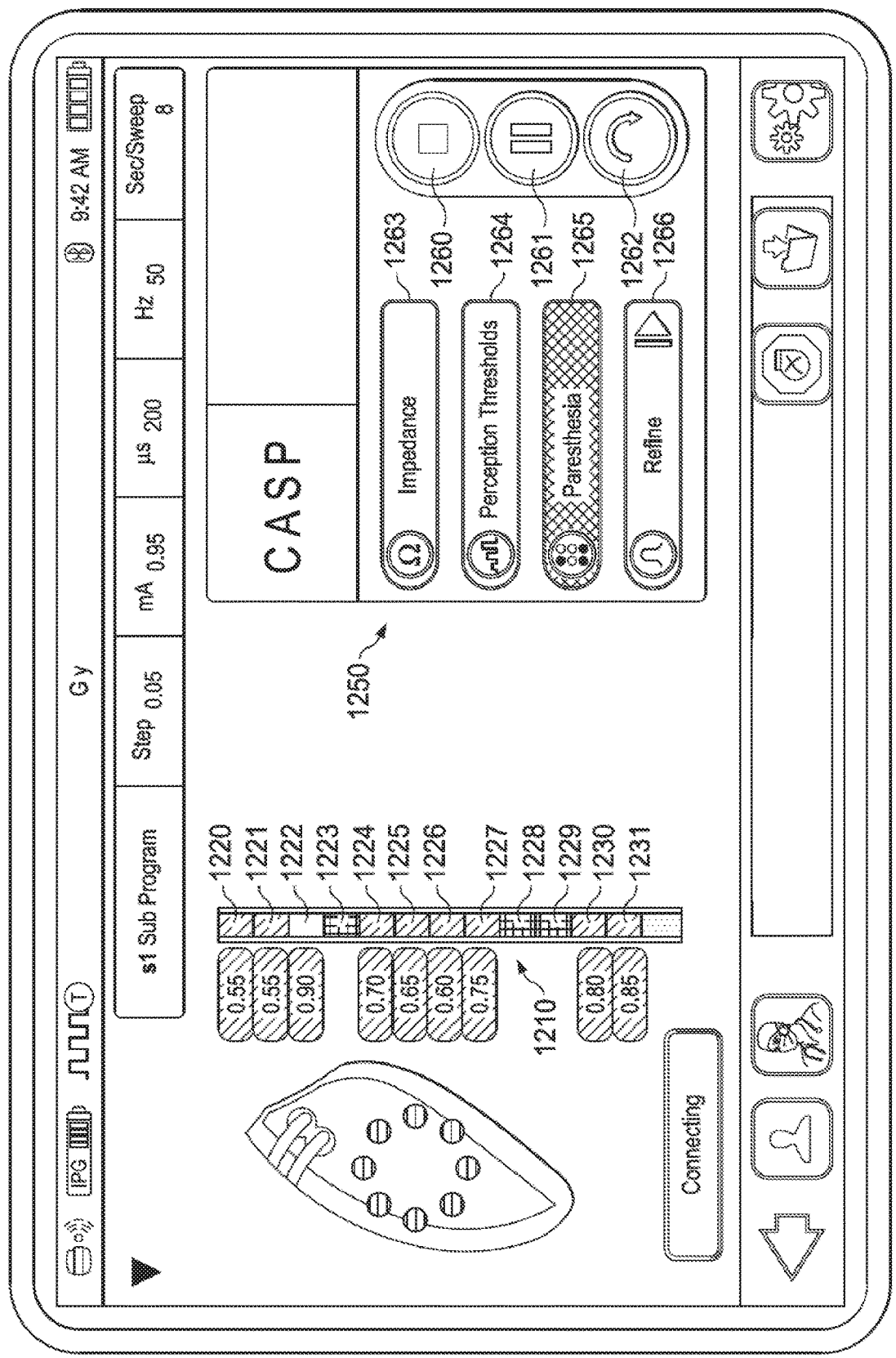
Figure 29:
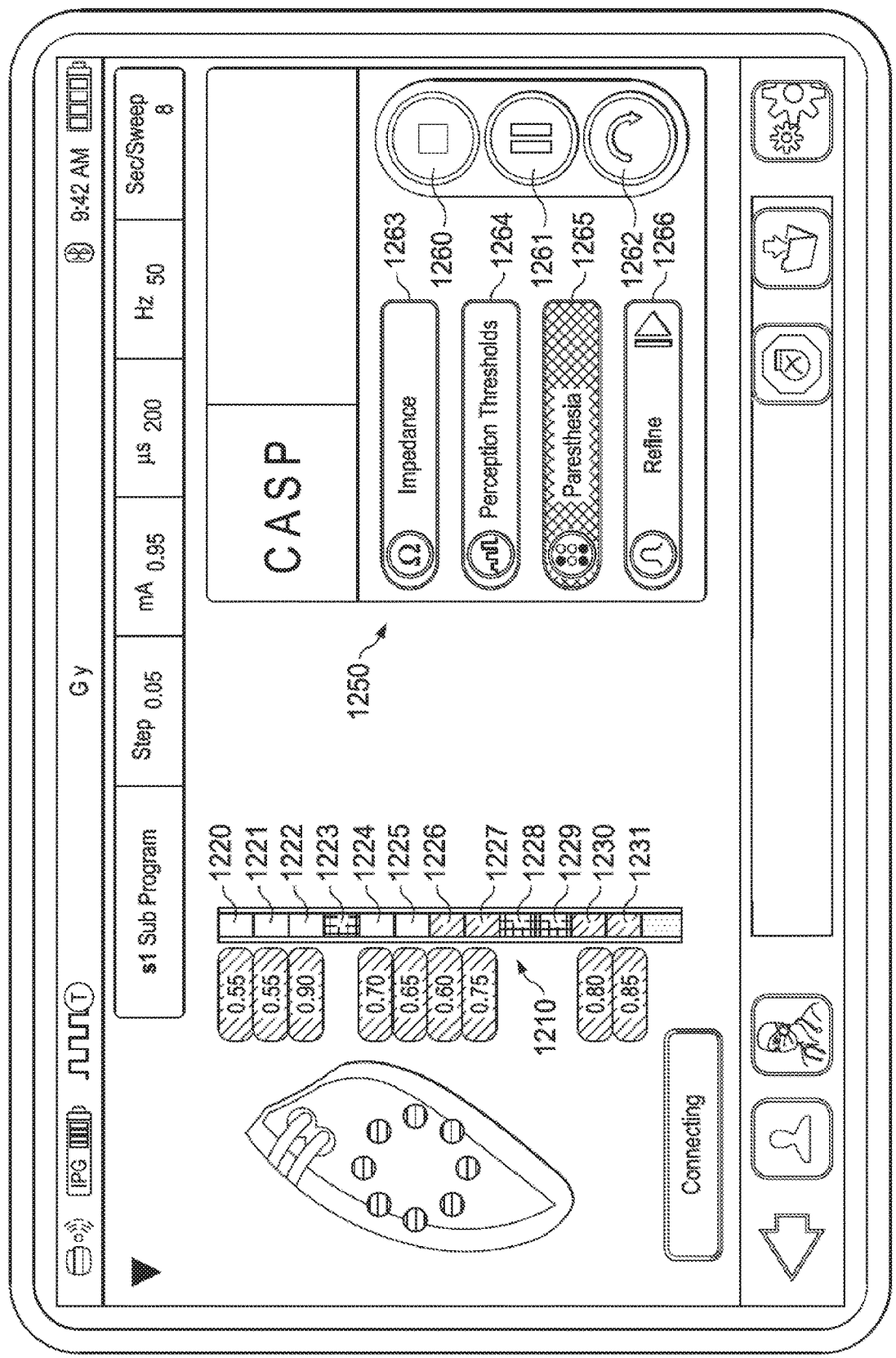

Referring now to FIGS. 28-29, after the perception threshold sweep is completed, the pain area sweep (also interchangeably referred to as the Paresthesia sweep hereinafter) starts. In a conventional CASP process illustrated in FIG. 28, since the contacts are swept individually, each activated contact will be visually distinguished one at a time, for example by individually flashing each activated contact (or giving a particular color or shading to the activated contact). In this example, the contact 1222 is activated to determine whether it produces Paresthesia for the patient, and therefore the contact 1222 is flashing.

In an alternative CASP process illustrated in FIG. 29, the contacts are divided into groups and then swept one group at a time. For example, the contacts 1220-1222 and 1224-1225 are grouped together and are all activated to their respective perception thresholds. These activated contacts 1220-1222 and 1224-1225 may be visually distinguished, for example by collectively flashing as a group or being collectively given a particular color or shading. Meanwhile, the rest of the contacts (either "bad" contacts or inactive contacts) are not flashing, which indicates that they are not being activated. As is shown in FIGS. 28-29, the numeric values of the perception thresholds for the contacts may be displayed adjacent thereto during the Paresthesia sweep as well.

Figure 30:
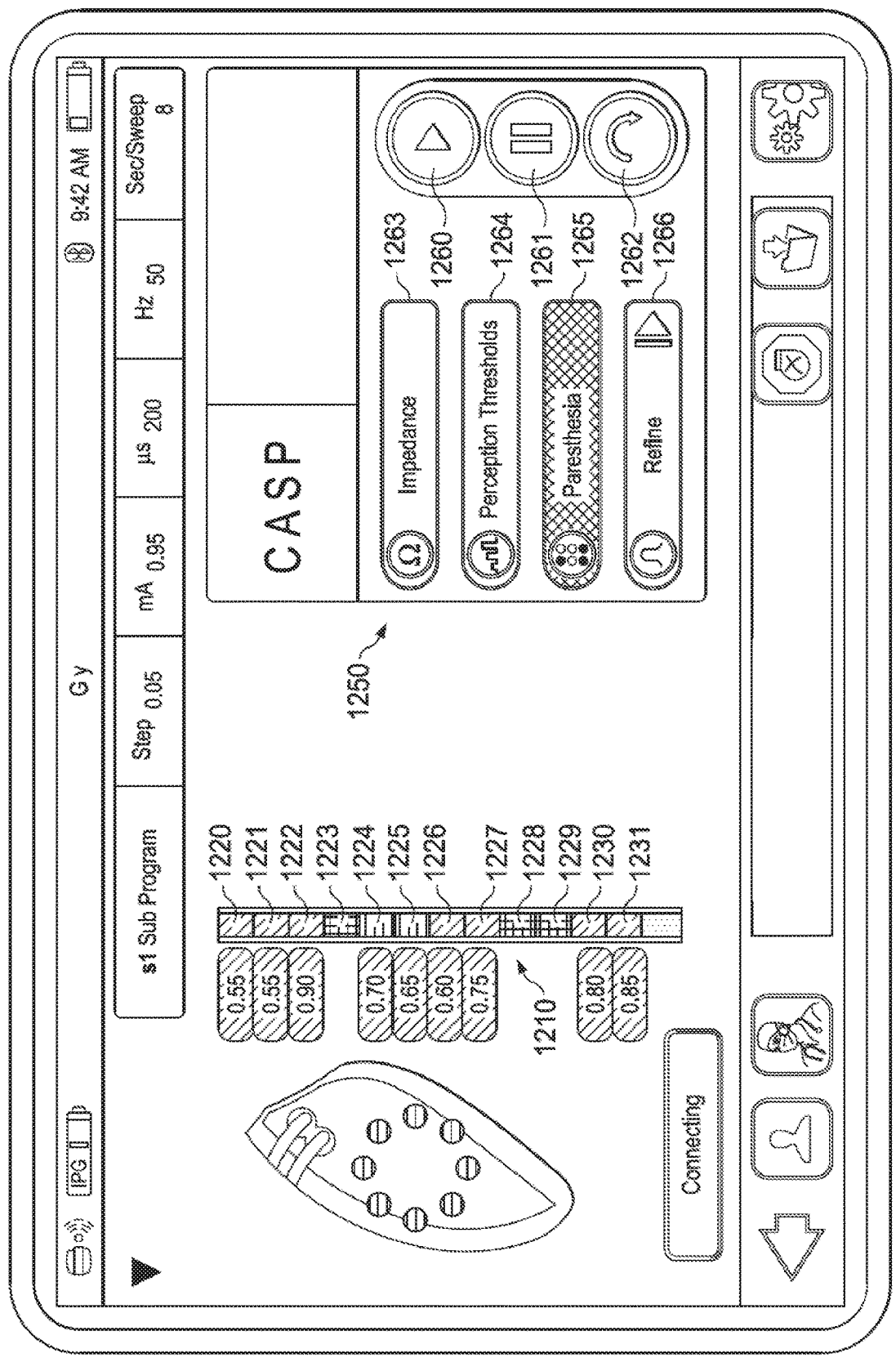

Referring now to FIG. 30, suppose that, after the completion of the pain area sweep or Paresthesia sweep, the contacts 1224 and 1225 have been identified as the Paresthesia-producing contacts. Thus, the contacts 1224 and 1225 may be visually distinguished from the rest of the contacts. In this example, the Paresthesia-producing contacts 1224-1225 are colored in blue, whereas the contacts (i.e., contacts 1220-1222, 1226-1227, and 1230-1231) that do not produce Paresthesia but whose perception thresholds have been determined are colored in green, and the "bad" contacts that did not undergo the CASP or alternative CASP processes are colored in yellow. These visual distinctions help remind the user of the characteristics or properties of each contact, as do the respective perception threshold values displayed next to these contacts. In this manner, the user is provided with a "visual map" or "visual landscape" that helps him/her to quickly comprehend the state of the contacts on the lead. However, the particular colors, shading, or flashing discussed above are merely examples, and different manners of visual distinctions may be implemented in alternative embodiments.

It is also understood that the execution of the three sweeps (impedance, perception threshold, and pain area) are sequential. In other words, the impedance sweep should be executed first, followed by the perception threshold sweep, and then the pain area sweep. The engagement of the virtual button 1260 may automatically trigger the execution of these sweeps, beginning with the impedance sweep. With reference to FIGS. 26-30, it can be seen that the virtual buttons 1263-1265 are highlighted when their corresponding sweep is being executed. In addition, prior to the completion of a particular sweep, the virtual button corresponding to a subsequent sweep is grayed-out and cannot be engaged. For example, as shown in FIG. 26, since the perception threshold sweep is still underway, the virtual button 1265 corresponding to the Paresthesia sweep is grayed-out and cannot be engaged by the user. This helps reduce user confusion or error arising from attempting to perform a sweep out of order.

However, after a particular sweep has been completed, the user may engage the corresponding virtual button to repeat such sweep. For example, as shown in FIGS. 26-30, since the impedance sweep has already been performed, the virtual button 1263 corresponding to the impedance sweep is not grayed-out, and a user engagement of the virtual button 1263 may repeat the impedance sweep. Similarly, as shown in FIG. 29 or 30, the perception threshold sweep has already been completed. Thus, the virtual button 1264 corresponding to the perception threshold sweep is not grayed out, and a user engagement of the virtual button 1264 may repeat the perception threshold sweep. In addition, as discussed above, the user may engage the virtual button 1262 to enter a debug-like mode where the execution for any sweep may be temporarily paused and stepped through one step at a time.

When all the sweeps have been completed and the target Paresthesia-producing contacts have been identified, the virtual button 1266 may also be used to save the information gathered through the CASP or alternative CASP processes. Such information may include, but is not limited to: which contacts are "good" or "bad", the perception thresholds for each "good" contact, and which contacts are the Paresthesia-producing contacts. This information may be saved locally on the clinician programmer or remotely to a server. This information may also be electronically transferred to the IPG later, for example in the form of an automatically-generated stimulation program that utilizes the information to configure its stimulation parameters. The user may also be allowed to manually adjust the information gathered herein by engaging the virtual button 1266. Alternatively, the user may discard the information and begin a new round of CASP or alternative CASP.

Figure 31:
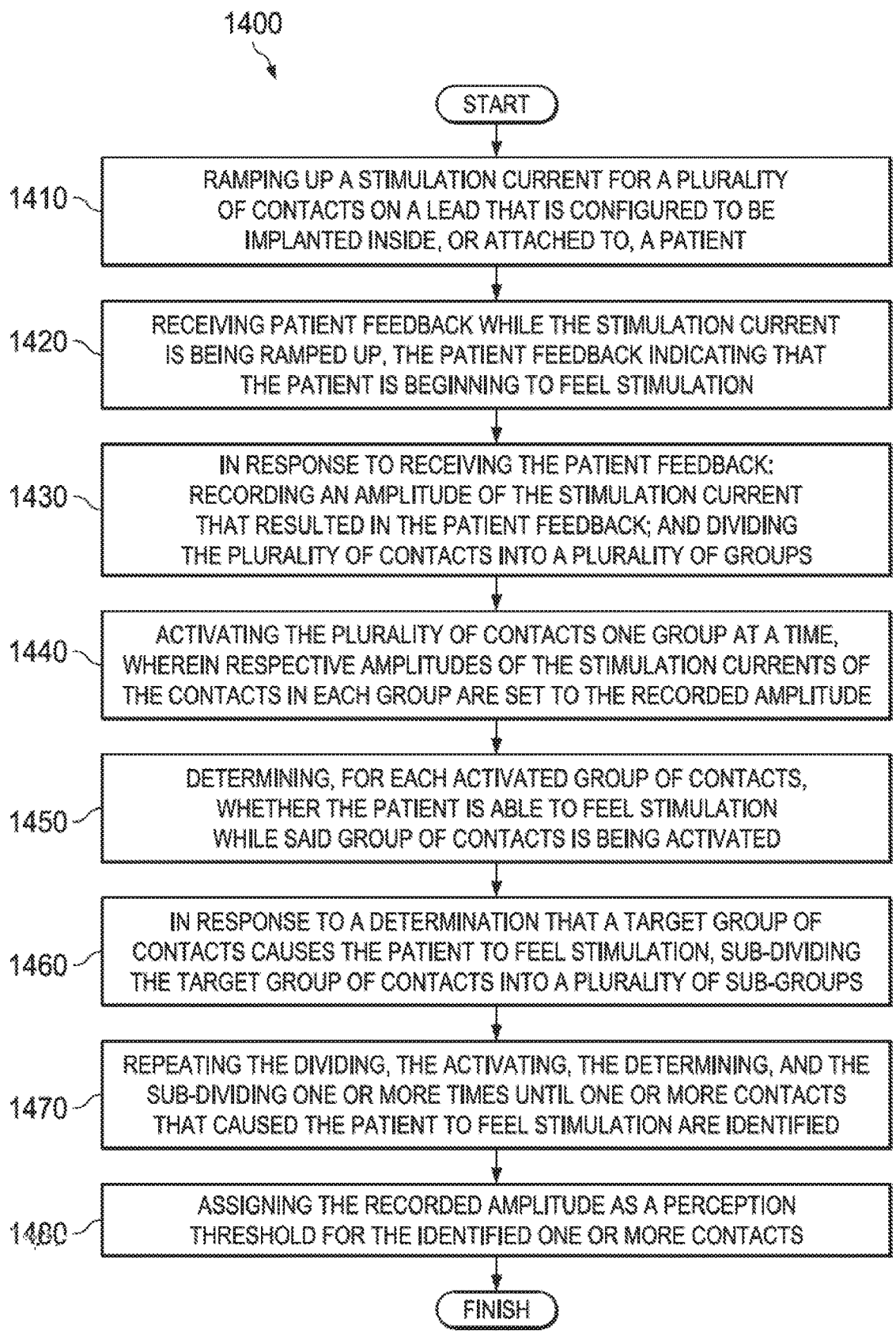

FIG. 31 is a flowchart of a method 1400 for performing the alternative CASP process discussed herein. The various steps of the method 1400 may be performed by one or more electronic processors, for example the electronic processors of a clinician programmer.

The method 1400 includes a step 1410 of ramping up a stimulation current for a plurality of contacts on a lead that is configured to be implanted inside, or attached to, a patient. In some embodiments, the ramping up comprises ramping up the stimulation current from zero. In some embodiments, the ramping up comprises ramping up the stimulation current for all contacts on the lead.

The method 1400 includes a step 1420 of receiving patient feedback while the stimulation current is being ramped up. The patient feedback indicates that the patient is beginning to feel stimulation. In some embodiments, step 1420 is carried out at least in part by an electronic patient feedback device. For example, the patient feedback is received by the electronic patient feedback device, which then reports the patient feedback to the clinician programmer.

The method 1400 includes a step 1430 of, in response to receiving the patient feedback: recording an amplitude of the stimulation current that resulted in the patient feedback; and dividing the plurality of contacts into a plurality of groups.

The method 1400 includes a step 1440 of activating the plurality of contacts one group at a time. The respective amplitudes of the stimulation currents of the contacts in each group are set to the recorded amplitude. In some embodiments, The method 1400 includes a step 1450 of determining, for each activated group of contacts, whether the patient is able to feel stimulation while said group of contacts is being activated. In some embodiments, the step 1450 comprises receiving further patient feedback via the electronic patient feedback device while at least one of the groups of contacts is being activated.

The method 1400 includes a step 1460 of, in response to a determination that a target group of contacts causes the patient to feel stimulation: sub-dividing the target group of contacts into a plurality of sub-groups.

The method 1400 includes a step 1470 of repeating the dividing, the activating, the determining, and the sub-dividing one or more times until one or more contacts that caused the patient to feel stimulation are identified.

The method 1400 includes a step 1480 of assigning the recorded amplitude as a perception threshold for the identified one or more contacts.

It is understood that the method 1400 may include additional steps that may be performed before, during, or after the steps 1410-1480 discussed above. For example, in some embodiments, the method 1400 further includes the following steps: before the ramping up, performing an impedance sweep for all contacts on the lead; determining which contacts have connections problems based on the impedance sweep; and selecting contacts that do not have connection problems as the plurality of contacts for which the ramping up is to be performed.

As another example, in some embodiments, the method 1400 further includes the following steps: repeating the ramping up, the receiving of the patient feedback, the recording of the amplitude, the dividing, the activating, the determining, the sub-dividing, the repeating, and the assigning one or more cycles until respective perception thresholds have been assigned for all contacts in the plurality of contacts. For each new cycle: the ramping up comprises resuming the ramping up of the stimulation current from the recorded amplitude from a previous cycle; and the one or more contacts whose perception thresholds have been assigned from the previous cycle are excluded from the new cycle. In some embodiments, the method 1400 further includes, after the respective perception thresholds have been assigned for all contacts in the plurality of contacts, identifying a subset of the contacts that produce Paresthesia for the patient. In some embodiments, the method 1400 further includes, developing a stimulation therapy for treating the patient based on at least one of: the subset of the contacts that produce Paresthesia for the patient or the respective perception thresholds assigned to each contact. In some embodiments, the method 1400 further includes, displaying, through the graphical user interface, the contacts that are being ramped up with a first visual characteristic; displaying, through the graphical user interface, the contacts for which the respective perception thresholds have been determined with a second visual characteristic; and displaying, through the graphical user interface, the contacts that produce Paresthesia with a third visual characteristic; wherein the first, second, and third visual characteristics are different from one another. For reasons of simplicity, additional steps of the method 1400 are not specifically discussed herein.

For the CASP and alternative CASP processes discussed above, the ramping up of the stimulation current need not be from zero. Instead, a non-zero starting value that is customized to the patient may be used to begin the ramping up process in CASP. For example, in an intra-op procedure, the healthcare professional may determine what the customized non-zero starting value for CASP should be based on the patient's response to stimulation. In more detail, suppose a lead such as the lead 1210 (discussed above with reference to FIG. 26) having twelve contacts is implanted inside the patient (e.g., along or near the spinal cord). To get a rough idea of what level of stimulation is needed to stimulate the patient, the healthcare professional may apply test stimulation with the top electrode 1220, or the bottom electrode 1231, or one of the middle electrodes 1225 or 1226, or combinations thereof.

Suppose the top electrode 1220 is used, the stimulation current amplitude delivered through that top electrode 1220 may be ramped up from a low value (such as 0.5 mA) toward a predefined maximum limit (e.g., 10 mA). The stimulation current may be steadily ramped up until the patient indicates a response to the test stimulation. The patient response may be done via the PFD 145 discussed above, or via verbal or physical feedback from the patient directly. Note that the patient's response to the test stimulation may not necessarily correspond to the "correct" or target area of stimulation. For example, the goal of the stimulation therapy is to treat the patient's lower left leg, but the patient may be indicating that he feels something in his right arm. This indicates that the lead has not been implanted correctly. Thus, the healthcare professional will have to adjust the lead location and re-apply the test stimulation.

During this process discussed above, the healthcare professional may get an idea of what value of stimulation current is likely to trigger a response from the patient, even if the response is not at the target area. For example, suppose that at 1.5 mA of stimulation from the top electrode 1220, the patient responds to the stimulation (intending to target the lower left leg) by informing the healthcare professional that he is feeling something in the right arm. After the lead has been repositioned, or perhaps the bottom electrode 1231 has been used to deliver the test stimulation without repositioning the lead, the patient now indicates that he is experiencing something in his left arm at 1.4 mA of stimulation. Eventually, the patient may respond that he is feeling something in his lower left leg at 1.6 mA of test stimulation out of the middle electrode 1225. The healthcare professional may determine that the patient is likely to respond to stimulation around 1.4 mA-1.6 mA. Accordingly, the healthcare professional may specify that the non-zero starting value for CASP should be set near 1.4 mA or 1.6 mA. In some embodiments, the non-zero starting value for CASP may be set as the lowest of the various stimulation current values that triggered a patient response, which in this above example is 1.4 mA. In other embodiments, the non-zero starting value for CASP may be set as the average of the various stimulation current values that triggered a patient response, which in this above example is 1.5 mA. In yet other embodiments, the non-zero starting value for CASP may be either the lowest value or the average value subtracted by a predefined number (e.g., 0.2 mA). Thus, the non-zero starting value for CASP may be 1.4 mA-0.2 mA=1.2 mA, or it may be 1.5 mA-0.2 mA=1.3 mA.

In all of these embodiments, the non-zero starting value for CASP is still customized to the patient, since these values are derived based on the patient's responses to test stimulation. This would vary from patient to patient, since another patient may respond to an entirely different set of stimulation current amplitudes.

In some embodiments, the user interface 1200 of the clinician programmer allows the healthcare professional to manually specify the non-zero starting value for CASP. As shown in FIG. 32, the healthcare professional may manually type in the non-zero starting value for CASP (such as 1.4 mA) into an entry field 1500, based on the testing results from the intra-op lead placement. Alternatively, the clinician programmer may record these different results discussed above, including the patient's responses and their corresponding stimulation current amplitudes. The clinician programmer may then automatically calculate and recommend a starting value (e.g., 1.5 mA) for CASP in another entry field 1510, also shown in FIG. 32. The recommended non-zero starting value for CASP may be calculated by taking the lowest of the stimulation current values that triggered a patient response, or an average of the stimulation current values that triggered a patient response, or the lowest value or average value subtracted by a predefined number, as discussed above. Furthermore, the user interface 1200 may allow the healthcare professional to manually adjust the starting value for CASP via a virtual control mechanism 1550, where an up arrow increases the starting value for CASP by a predefined step (e.g., 0.1 mA), and a down arrow decreases the starting value for CASP by the predefined step.

In some other embodiments, a closed loop system may be used to determine the non-zero starting value for performing CASP. In more detail, sensing electrodes may be used to sense evoked potentials generated in response to electrical stimulation, where the evoked potentials serve as an indication that the patient is about to feel the electrical stimulation (or is feeling the stimulation). An evoked potential or evoked potential signal is an integrated measurement of the conducted action potentials of a collection of nerves in response to stimulation. Among other things, the evoked potential signal can reflect the number of neurons activated, the fiber diameter of neurons that have been activated, the conduction velocity of the activated neurons, etc. For the purposes of the present disclosure, the terms "evoked potentials" and "action potentials" or "evoked action potentials" may be used interchangeably.

Figure 33A:
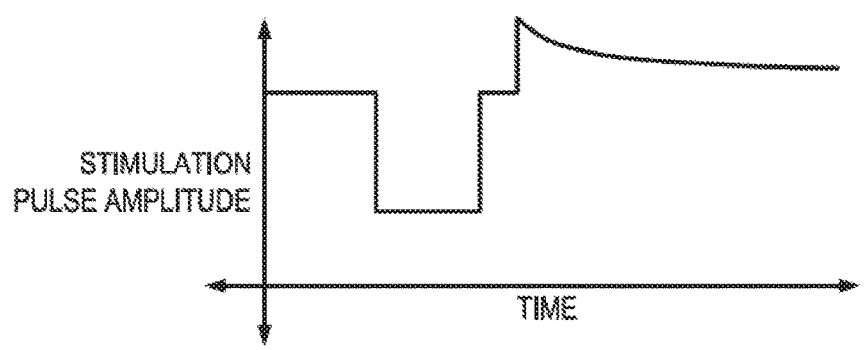
FIGS. 33A, 33B, and 33C are various graphs illustrating the stimulation pulse amplitude, evoked potential amplitude, and evoked potential V.S. stimulation pulse amplitude according to embodiments of the present disclosure.
Figure 33B:
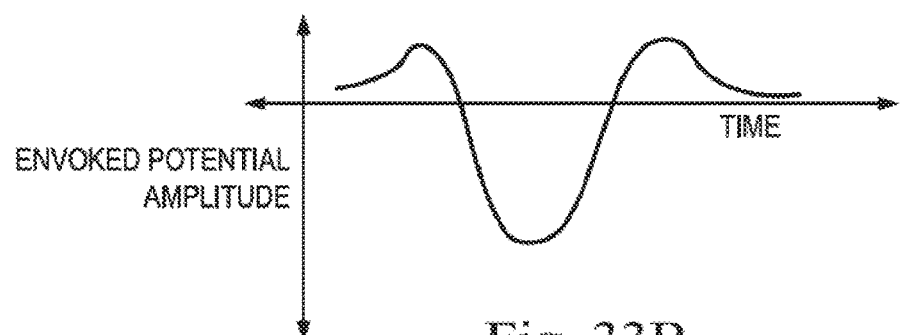
Figure 33C:
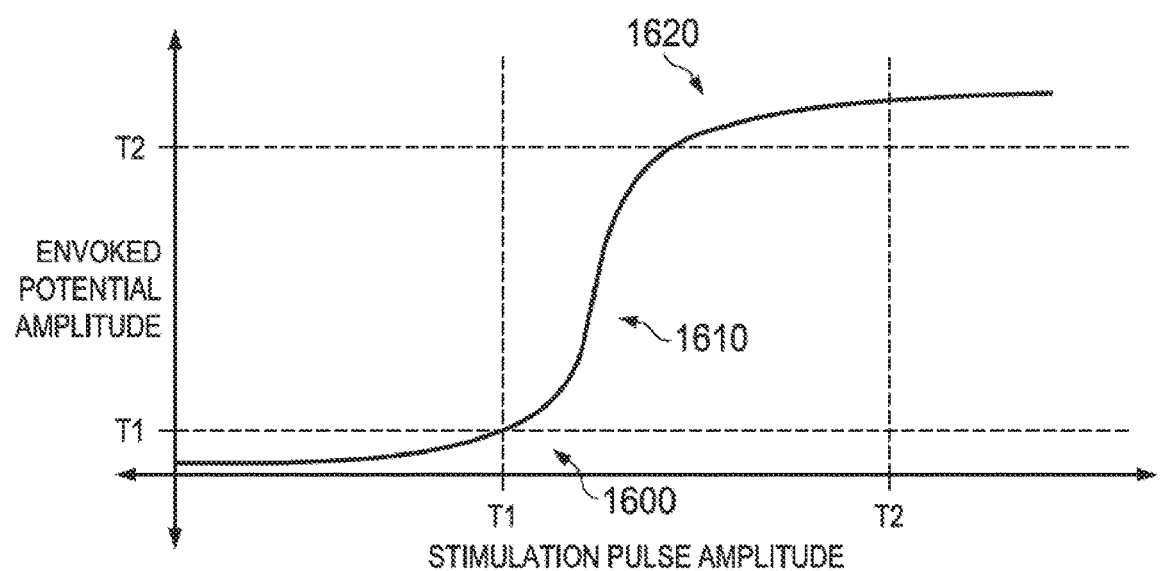
Figure 34:
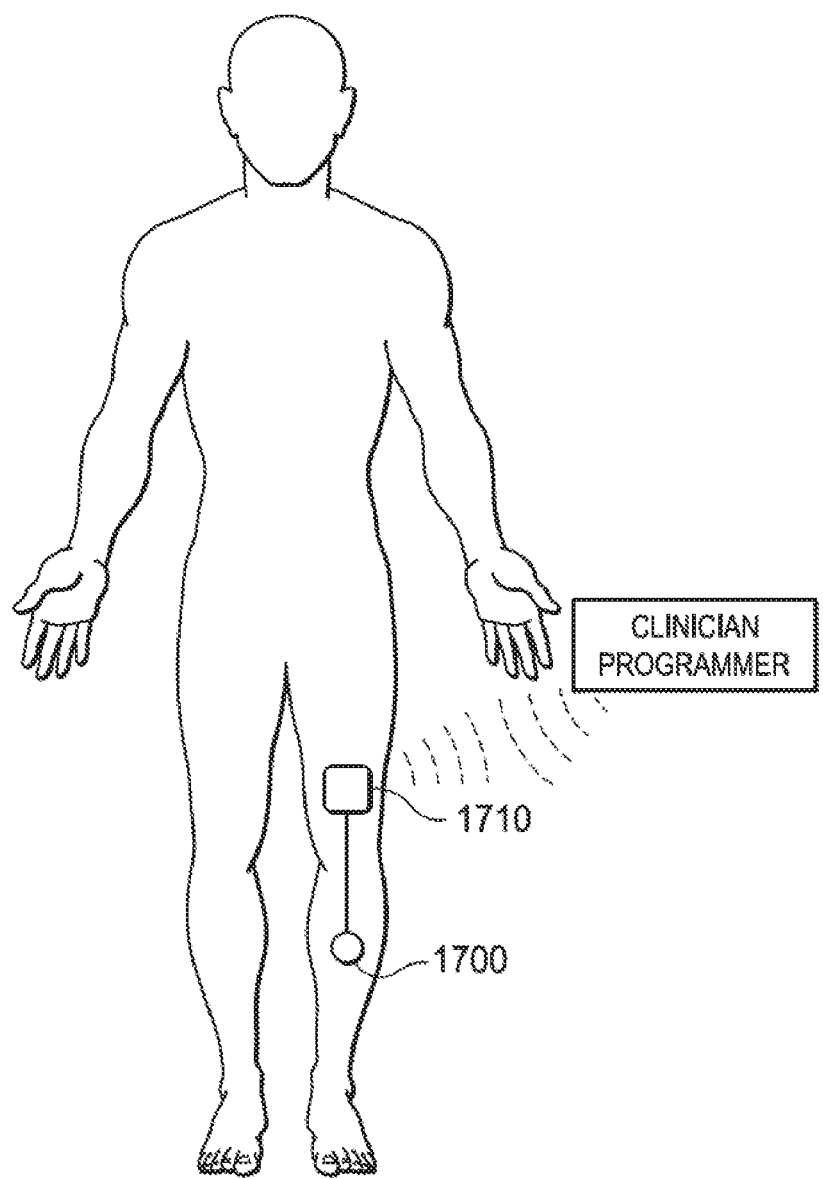
FIG. 34 illustrates a simplified closed-loop system of using sensing electrodes to measure evoked potential according to embodiments of the present disclosure.

FIG. 33A illustrates a simplified waveform of stimulation current amplitude versus time, FIG. 33B illustrates a simplified waveform of evoked potential versus time, and FIG. 33C illustrates a simplified waveform of evoked potential amplitude versus stimulation current amplitude.

Test stimulation is generated by a pulse generator (such as an IPG or an EPG) and delivered to a target nerve site via one or more electrodes of the lead 1210, for example via the top electrode 1220, or the bottom electrode 1231, or one of the middle electrodes 1225 or 1226, or combinations thereof. As a part of this process, a stimulation parameter (e.g., stimulation current) is being ramped up in value. For example, the ramping up may include steadily increasing the value of the stimulation parameter by a small predetermined step size (0.1 mA). In the illustrated embodiment, the stimulation parameter is stimulation pulse (as an electrical current) amplitude. In other embodiments, the stimulation parameter may include a pulse width.

As shown in FIG. 33C, in a first region 1600, as the value of the stimulation parameter is being ramped up, the evoked potential barely changes initially. In other words, up to a first threshold T1, the evoked potential may appear noise-like. However, after the first threshold T1, the evoked potential begins increasing rapidly as stimulation amplitude increases, either in a linear manner or an exponential manner. This is shown in region 1610 in FIG. 33C. This behavior may continue for a while, until another threshold T2 is reached, after which the evoked action potential does not increase much (if at all) even as stimulation amplitude continues to increase. This is shown in region 1620 in FIG. 33C.

According to the various aspects of the present disclosure, the amount of evoked potential in response to the stimulation is detected by sensing electrodes (discussed in more detail below) and communicated back to the clinician programmer. Based on the behavior of the detected evoked potential, the clinician programmer can evaluate whether the region 1610 has been reached. For example, if the amplitude of the evoked potential increases significantly (e.g., greater than 20%) from the previous measurement, then it may be deemed that the region 1610 has been reached, or that the threshold T1 has been crossed over. The stimulation amplitude corresponding to T1 is then recorded by the clinician programmer as a non-zero starting value for CASP.

The rationale for basing the non-zero starting value for CASP as a function of the evoked potential is that the rapid increase of the evoked potential (e.g., the beginning of region 1610) is generally associated with the perception threshold in which the patient actually experiences stimulation. In some cases, the evoked potential may begin increasing rapidly in region 1610 right before the patient actually experiences stimulation. In other cases, the rapid increase in evoked potential may occur almost simultaneously with the patient experiencing stimulation. Thus, the value of the stimulation amplitude at T1 (i.e., beginning of the region 1610) can be loosely used as a surrogate of the perception threshold. In some embodiments, to ensure that the perception threshold is not missed, the clinician programmer may set the non-zero value for starting CASP to be a value slightly lower than the value of the stimulation amplitude corresponding to T1. For example, if the stimulation amplitude corresponding to T1 is 1.5 mA, then the clinician programmer may set the starting value for CASP to be 0.2 (or 0.1, or 0.3, or another suitable number) less than 1.5 mA, which would result in a value of 1.3 mA in this example.

Again, regardless of whether the starting value for CASP is set to be the value (1.5 mA) directly corresponding to T1, or another value that is a function of the value corresponding to T1 (e.g., 1.5−0.2=1.3 mA), that value is still customized for that specific patient. Each patient may exhibit a different "evoked potential VS stimulation" response. In other words, the graph shown in FIG. 33C may vary from patient to patient. Thus, the measured evoked potential and the stimulation amplitude value corresponding thereto may be unique to the patient and as such can be used as a customized starting value for CASP for that patient.

The configuration for performing the "closed loop" evoked potential measurement is now discussed in more detail. In some embodiments, the sensing electrodes are the electrodes on the lead 1210 that are not being configured to deliver electrical stimulation. Thus, if the top electrode 1220 is being configured to deliver electrical stimulation, then the rest of the electrodes 1221-1231 may each be used as a sensing electrode. Similarly, if the top electrode 1220, the bottom electrode 1231, and the middle electrode 1225 are all configured as stimulating electrodes, then the rest of the electrodes 1221-1224 and 1226-1230 may each be used as a sensing electrode. In conjunction with measurement circuitry, these sensing electrodes may sense the evoked action potentials and communicate the sensed evoked potentials back to the clinician programmer. In some embodiments, the measurement circuitry may include amplifiers and may be implemented within the stimulation ASIC 230 of the IPG discussed above with reference to FIG. 8. In other embodiments, the measurement circuitry may be implemented separately from the ASIC 230, but may be still implemented inside the IPG. In yet other embodiments, the measurement circuitry may be implemented on the lead itself, for example on the lead 1000 or 1210 discussed above.

In some embodiments, the sensing electrodes may also include electrodes separate from the electrodes on a lead (e.g., separate from the electrodes 1220-1231 on the lead 1210). Referring now to FIG. 33, one or more sensing electrodes 1700 (separate from the stimulation lead) may be deployed on different regions of the patient's body. These sensing electrodes 1700 can also sense the evoked action potentials and send the sensing result to the clinician programmer, for example through sensing circuitry implemented on the sensing electrodes 1700 or on a separate electronic device 1710 coupled to the sensing electrodes 1700. In addition to sensing circuitry, the electronic device 1710 includes telecommunication circuitry such as transceivers configured to conduct telecommunications under Wi-Fi, Bluetooth, or MICS, so that it can communicate with the clinician programmer accordingly. As such, the clinician programmer may still determine the value of the stimulation amplitude that caused the evoked potential to rapidly increase, and that value of the stimulation amplitude (or a function thereof) may be used as a customized starting value for CASP.

Figure 35:
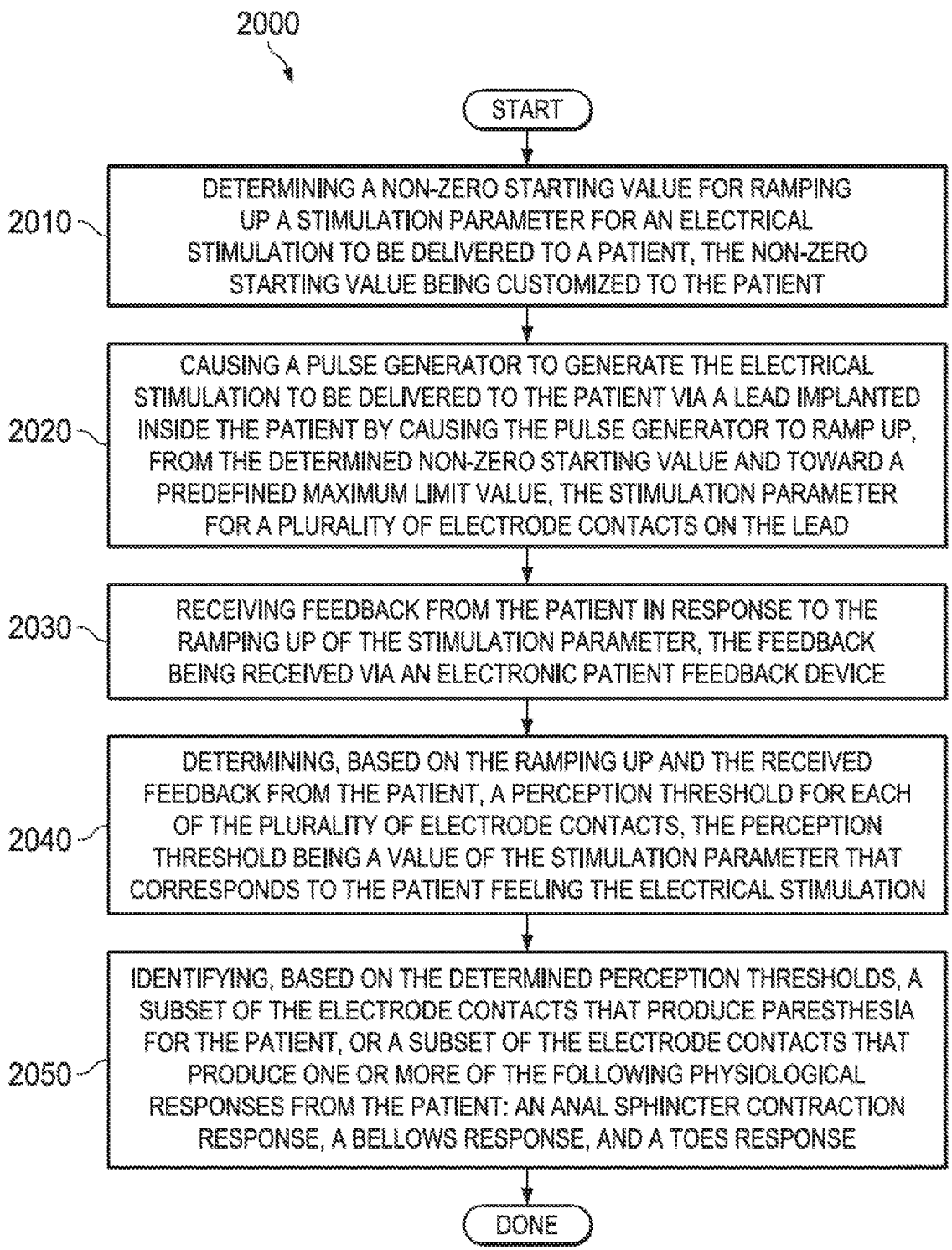

FIG. 35 is a flowchart of a method 2000 for performing a computer-assisted stimulation programming process discussed herein. The various steps of the method 2000 may be performed by one or more electronic processors, for example the electronic processors of a clinician programmer.

The method 2000 includes a step 2010 of determining a non-zero starting value for ramping up a stimulation parameter for an electrical stimulation to be delivered to a patient. The non-zero starting value is customized to the patient. In some embodiments, the determining the customized starting value comprises the following steps: increasing the stimulation parameter for at least one electrode contact on the lead from a value lower than the customized starting value; detecting an evoked action potential in response to the increasing of the stimulation parameter; and recording a value of the stimulation parameter that corresponds to the evoked action potential as the customized starting value. In some embodiments, the at least one electrode contact comprises a top electrode contact on the lead, a bottom electrode contact on the lead, or a middle electrode contact on the lead. In some embodiments, the determining the non-zero starting value comprises one of: receiving a specified non-zero starting value from a healthcare professional, or calculating the non-zero starting value based on one or more patient responses to test stimulation.

The method 2000 includes a step 2020 of causing a pulse generator to generate the electrical stimulation to be delivered to the patient via a lead implanted inside the patient by causing the pulse generator to generate the electrical stimulation comprises causing the pulse generator to ramp up, from the determined non-zero starting value and toward a predefined maximum limit value, the stimulation parameter for a plurality of electrode contacts on the lead. In some embodiments, the causing the pulse generator to ramp up the stimulation parameter comprises causing the pulse generator to ramp up a stimulation current as the stimulation parameter.

The method 2000 includes a step 2030 of receiving feedback from the patient in response to the ramping up of the stimulation parameter. The feedback may be received via an electronic patient feedback device, such as the PFD discussed above with reference to FIGS. 1 and 5-7.

The method 2000 includes a step 2040 of determining, based on the ramping up and the received feedback from the patient, a perception threshold for each of the plurality of electrode contacts. The perception threshold is a value of the stimulation parameter that corresponds to the patient feeling the electrical stimulation.

The method 2000 includes a step 2050 of identifying, based on the determined perception thresholds, a subset of the electrode contacts that produce paresthesia for the patient, or a subset of the electrode contacts that produce one or more of the following physiological responses from the patient: an anal sphincter contraction response, a bellows response, and a toes response.

It is understood that the method 2000 may include additional steps that may be performed before, during, or after the steps 2010-2050 discussed above. For example, in some embodiments, the method 200 further includes a step of developing a stimulation protocol based on the perception threshold or on the paresthesia.

The CASP process and alternative CASP process discussed above offers various advantages. Of course, it is understood that different embodiments may offer different advantages, not all advantages are necessarily discussed herein, and no particular advantage is required for all embodiments. One of the advantages is that the CASP and alternative CASP processes can identify the optimal contacts for treating pain. For example, the pain area sweep discussed above can pinpoint the one or more contacts that offer the best pain relief in the target pain areas.

Another advantage is that the perception threshold for each contact may be quickly determined. Ideally, one or two contacts may be all that are needed to provide sufficient electrical stimulation to treat each area of pain for the patient. If a successful surgery is performed, all the contacts on the lead should be placed at or near the target nerve tissues that offer pain relief when stimulated (e.g., causing Paresthesia). Suppose contacts 5 and 6 in a lead containing 12 contacts are identified as the best contacts for producing pain relief. As such, contacts 5 and 6 are activated to provide electrical stimulation. However, over time, the positioning for the contacts on the lead may migrate or drift. When this occurs, the contacts 5 and 6 may no longer be the best pain-relief contacts. For example, they may have drifted away from the target nerve tissue. Therefore, new best pain-relief contacts need to be identified. Suppose contacts 2 and 3 are now identified as the best pain-relief contacts. At this point, the suitable stimulation current for contacts 2 and 3 are already known, because their respective perception thresholds had already been determined in the CASP process performed during exploratory or permanent surgery. Alternatively, the remaining contacts may each be activated with their respective previously-determined perception threshold stimulation currents in order to pinpoint the new best pain-relief contacts. Regardless, the CASP and alternative CASP processes result in a map or chart of the "correct" amount of stimulation current to effectively stimulate each contact (for the contact to produce a stimulation sensation), and this map/chart facilitates the creation of new stimulation protocols and/or the modification of existing stimulation protocols.

Yet another advantage is that the CASP and alternative processes can be performed in a relatively short period of time (e.g., a few minutes), because the algorithms discussed above can be quickly executed by the computer processors of the clinician programmer or another suitable portable electronic device.

A further advantage is that starting CASP from a non-zero value will significantly reduce the amount of time needed to perform CASP. Rather than starting from zero, the present disclosure determines a non-zero starting value for CASP that is customized to the patient. This customized value should be pretty close to the value that corresponds to the perception threshold. For example, suppose the perception threshold is 2 mA. Starting CASP from zero and incrementing the current amplitude in 0.1 mA increments will take 20 iterations before the perception threshold is reached. According to the present disclosure, CASP may be started at a value greater than zero and lower than the perception threshold, for example at 1.5 mA based on either the specification from the healthcare professional or based on the closed loop system using sensing electrodes to sense the evoked potential. Now only 5 iterations are needed to reach the perception threshold. The significantly reduced time needed to perform CASP results in greater satisfaction for both the patient and the healthcare professional.

It is understood that, in addition to spinal cord stimulation, CASP may also be used in other neuromodulation contexts, such as peripheral nerve stimulation, pelvic (or sacral) nerve stimulation, or deep brain stimulation. For example, rather than using CASP to fine tune the stimulation therapy for treating patient (e.g., finding the best electrodes for generating comfortable paresthesia), CASP may be used in a pelvic stimulation context to identify electrodes or fine tune the therapy for generating the desired physiological responses, such as anal sphincter contraction or bellows and toes responses, which are discussed in greater detail in U.S. patent application Ser. No. 14/537,293, filed on Nov. 12, 2014, and entitled "IPG CONFIGURED TO DELIVER DIFFERENT PULSE REGIMES TO DIFFERENT LEADS" to Kaula et. al., the disclosure of which is hereby incorporated by reference in its entirety.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method, comprising:
    applying an electrical stimulation to a patient via a lead having one or more electrodes located thereon;
    increasing a stimulation parameter of the electrical stimulation, wherein the stimulation parameter includes stimulation amplitude, stimulation pulse width, or stimulation frequency;
    monitoring a variation of an evoked action potential while the stimulation parameter is being increased from a previous value to a current value;
    determining, based on the monitoring, an amount of increase between each evoked action potential corresponding to the current value of the stimulation parameter and a previous evoked action potential corresponding to the previous value of the stimulation parameter;
    determining, based on the amount of increase, whether a threshold of the evoked action potential has been reached; and
    in response to a determination that the threshold of the evoked action potential has been reached, recording a first value of the stimulation parameter that resulted in the threshold of the evoked action potential being reached.

2. The method of claim 1, further comprising: using the first value of the stimulation parameter in a computer assisted programming process in which the stimulation parameter is automatically adjusted by a computer processor.

3. The method of claim 2, wherein the using the first value comprises assigning the first value of the stimulation parameter as a starting value in the computer assisted programming process.

4. The method of claim 2, wherein the using the first value comprises:
    calculating a second value as a function of the first value; and
    assigning the second value as a starting value in the computer assisted programming process.

5. The method of claim 4, wherein the calculating the second value comprises subtracting the first value by a predetermined value, wherein the predetermined value is less than the first value.

6. The method of claim 2, further comprising: performing the computer assisted programming process to determine a perception threshold of the one or more electrodes of the lead.

7. The method of claim 1, wherein the monitoring comprises receiving the evoked action potential measured by one or more sensing electrodes.

8. The method of claim 7, wherein the one or more sensing electrodes are located separately from the lead.

9. The method of claim 8, wherein:
    the one or more electrodes include a plurality of electrodes;
    a first subset of the plurality of electrodes is used as stimulation electrodes to apply the electrical stimulation to the patient; and
    a second subset of the plurality of electrodes is used as the sensing electrodes to measure the evoked action potential.

10. The method of claim 1, wherein the determining whether the threshold of the evoked action potential has been reached comprises determining whether the rate of increase exhibits an exponential behavior.

11. The method of claim 1, wherein the applying, the increasing, the monitoring, the determining the amount of increase, the determining whether the threshold of the evoked action potential has been reached, and the recording are performed at least in part using an electronic programming device that is configured to program a pulse generator to generate the electrical stimulation.

12. The method of claim 1, further comprising: repeating the applying, the increasing, the monitoring, the determining the amount of increase, the determining whether the threshold of the evoked action potential has been reached, and the recording for each of a plurality of patients, thereby obtaining a plurality of first values, wherein each of the first values is customized to a respective patient.

13. The method of claim 1, wherein the determining the amount of increase comprises determining a percentage increase from each evoked action potential and the previous evoked action potential.

14. A method, comprising:
applying an electrical stimulation to a patient via a lead having one or more electrodes located thereon;
increasing a stimulation parameter of the electrical stimulation, wherein the stimulation parameter includes stimulation amplitude, stimulation pulse width, or stimulation frequency;
measuring a change in an evoked action potential while the stimulation parameter is being increased from a previous value to a current value;
determining, based on the monitoring, an amount of increase between each evoked action potential corresponding to the current value of the stimulation parameter and a previous evoked action potential corresponding to the previous value of the stimulation parameter;
determining, based on the amount of increase, whether the evoked action potential has reached a predefined threshold;
in response to a determination that the predefined threshold of the evoked action potential has been reached, recording a first value of the stimulation parameter that resulted in the predefined threshold of the evoked action potential being reached;
calculating a starting value of a computer assisted stimulation programming process as a value that is equal to the first value or smaller than the first value by a predefined number, wherein the computer assisted stimulation programming process automatically adjusts the stimulation parameter via a computer processor;
performing the computer assisted stimulation programming process, wherein the computer assisted stimulation programming process comprises ramping up the stimulation parameter, for each of the electrodes, from the starting value toward a predetermined maximum value; and
determining a perception threshold for each of the electrodes based on the performing of the computer assisted stimulation programming process.

15. The method of claim 14, wherein the measuring comprises measuring the evoked action potential via one or more sensing electrodes that are located outside the lead.

16. A system, comprising:
a pulse generator configured to generate electrical stimulation;
a lead having a plurality of electrodes thereon and configured to deliver the electrical stimulation to a patient; and
an electronic programmer configured to perform operations comprising:
increasing a stimulation parameter of the electrical stimulation, wherein the stimulation parameter includes stimulation amplitude, stimulation pulse width, or stimulation frequency;
monitoring, via a subset of the electrodes as sensing electrodes or using one or more external electrodes as the sensing electrodes, an evoked action potential while the stimulation parameter is being increased from a previous value to a current value;
determining, based on the monitoring, an amount of increase between each evoked action potential corresponding to the current value of the stimulation parameter and a previous evoked action potential corresponding to the previous value of the stimulation parameter;
determining, based on the amount of increase, whether a threshold of the evoked action potential has been reached; and
in response to a determination that the threshold of the evoked action potential has been reached, recording a first value of the stimulation parameter that resulted in the threshold of the evoked action potential being reached.

17. The system of claim 16, wherein the operations further comprise: performing a computer assisted programming process in which the first value or a second value is used as a starting value of the stimulation parameter, wherein the second value is less than the first value by a predetermined amount, wherein the computer assisted stimulation programming process automatically adjusts the stimulation parameter via a computer processor.

18. The system of claim 17, wherein the operations further comprise: determining a perception threshold of the one or more electrodes of the lead based on the computer assisted programming process.

19. The system of claim 16, wherein the determining whether the threshold of the evoked action potential has been reached comprises determining whether the amount of increase is greater than a predefined amount of increase.

20. The system of claim 16, wherein the determining the amount of increase comprises determining a percentage increase from each evoked action potential and the previous evoked action potential.

* * * * *